US006191156B1

(12) United States Patent
Kifor et al.

(10) Patent No.: US 6,191,156 B1
(45) Date of Patent: Feb. 20, 2001

(54) COMPOSITIONS AND METHODS FOR TREATING BLADDER DYSFUNCTION

(75) Inventors: Imre Kifor, Methuen; Gordon Williams, Belmont; Maryrose P. Sullivan, Quincy, all of MA (US)

(73) Assignee: The Brigham and Women's Hospital, Inc., Boston, MA (US)

( * ) Notice: Under 35 U.S.C. 154(b), the term of this patent shall be extended for 0 days.

(21) Appl. No.: 09/047,562

(22) Filed: Mar. 25, 1998

Related U.S. Application Data
(60) Provisional application No. 60/041,874, filed on Apr. 11, 1997, and provisional application No. 60/041,875, filed on Apr. 11, 1997.

(51) Int. Cl.$^7$ .................................................. A61K 31/14

(52) U.S. Cl. .............................. 514/381; 514/15; 514/16; 514/316; 514/327; 514/328; 514/303; 514/311; 514/381

(58) Field of Search .............................. 514/381, 15, 116, 514/316, 327, 328, 303, 311, 387

(56) References Cited

U.S. PATENT DOCUMENTS

| | | | |
|---|---|---|---|
| 5,138,069 | * 8/1992 | Carini et al. | 548/253 |
| 5,266,583 | * 11/1993 | Ohtawa | 514/381 |
| 5,278,192 | 1/1994 | Fung et al. | 514/645 |
| 5,475,004 | 12/1995 | Heitsch et al. | 514/303 |
| 5,565,475 | * 10/1996 | Muhlhauser et al. | 514/342 |
| 5,631,284 | * 5/1997 | Legzdins et al. | 514/505 |
| 5,658,936 | 8/1997 | Kifor et al. | 514/381 |
| 5,712,287 | * 1/1998 | Muhlhauser et al. | 514/304 |
| 5,795,904 | * 8/1998 | Cohen et al. | 514/381 |

FOREIGN PATENT DOCUMENTS

| | | |
|---|---|---|
| WO97/10821 | 3/1997 | (WO) . |
| PCT/US98/05886 | 6/1998 | (WO) . |
| PCT/US98/05893 | 8/1998 | (WO) . |

OTHER PUBLICATIONS

Emil A. Tanagho, et al., "Urethral Resistance: Its Components and Implications," Investigative Urology, (1969) vol. 7, No. 2, pp. 136–149.

Gordon F. Anderson, et al., "Evidence for Angiotensin II Receptors in the Urinary Bladder of the Rabbit," Can. J. Physiol. Pharmacol. (1984) 62:390–395.

Fumiaki Marumo, "Enhancing Effects of Angiotensin I on the Vasopressin–Stimulated Water Flow of Toad Bladder Through Increased Cyclic AMP in Mucosal Cells," Life Sciences, (1986) vol. 39, pp. 2371–2375.

Earl Y. Cheng, et al., "Angiotensin II and Basic Fibroblast Growth Factor Induce Neonatal Bladder Stromal Cell Mitogenesis," J. Urol. (1996) vol. 156, pp. 593–597.

Christopher P. Steidle, et al., "Bradykinin–Induced Contractions of Canine Prostate and Bladder: Effect of Angiotensin–Converting Enzyme Inhibition," J. Urol., (1990) vol. 144, pp. 390–392.

Noureddine Rouissi, et al., "Inhibitors of Peptidases: How They Influence the Biological Activities of Substance P. Neurokinins, Bradykinin and Angiotensin in Guinea Pig, Hamster and Rat Urinary Bladders," Pharmacology (1990), vol. 40, pp. 196–204.

Geza Simon, et al., "Stimulation of Vascular Glycosaminoglycan Synthesis by Subpressor Angiotensin II in Rats," Hypertension (1994), vol. 23, Suppl. I, pp. I–148–I–151.

Nour–Eddine Rhaleb, et al., "DuP 753 Is a Specific Antagonist for the Angiotensin Receptor," Hypertension (1991), vol. 17, pp. 480–484.

Thomas E. Lohmeier, et al., "Renal Nerves Promote Sodium Excretion in Angiotensin–Induced Hypertension," Hypertension (1998), vol. 31 [part 2], pp. 429–434.

Nobuaki Tanabe, et al., "Angiotensin II Receptors in the Rat Urinary Bladder Smooth Muscle: Type I Subtype Receptors Mediate Contractile Responses," J. Urol. (1993) vol. 150, pp. 1056–1059.

Masahiko Saito, et al., "Response of the Human Urinary Bladder to Angiotensins: A Comparison Between Neurogenic and Control Bladders," J. Urol. (1993) vol. 149, pp. 408–411.

Lane S. Palmer, et al., "The Effect of Angiotensin Converting Enzyme Inhibition and Angiotensin II Receptor Antagonism on Obstructed Rat Bladder," J. Urol. (1997), vol. 158, pp. 1100–1104.

B.F. Lindberg, et al., "Angiotensin I is Converted to Angiotensin II by a Serine Protease in Human Detrusor Smooth Muscle," Am. J. Physiol, (1994) vol. 266, pp. R1861–R1867.

Dana Weaver–Osterholtz, et al., "The Urinary Bladder Angiotensin System: Response to Infusions of Angiotensin I and Angiotensin–Converting Enzyme Inhibitors," American Journal of Kidney Diseases, (1996), vol. 28, No. 4, pp. 603–609.

Tatsuo Morita, et al., "Intraarterial Infusion Chemotherapy with [Sar$^1$, Ile$^8$] Angiotensin II for Bladder Cancer," Am. J. Clin. Oncol. (CCT) (1992), vol. 15(3), pp. 188–193.

J.Y. Jeremy, et al., "Differential Changes of Adrenoceptor– and Muscarinic Receptor–Linked Prostacyclin Synthesis by the Aorta and Urinary Bladder of the Diabetic Rat," Br. J. Pharmacol. (1993), vol. 108, pp. 1131–1136.

(List continued on next page.)

Primary Examiner—James H. Reamer
(74) Attorney, Agent, or Firm—Wolf, Greenfield & Sacks, P.C.

(57) ABSTRACT

A method for treating patients having bladder dysfunction is described. The method involves the step of treating a patient with a renin-angiotensin system inhibitor. Preferably the inhibitor is an Angiotensin II antagonist, an ACE inhibitor, or a renin inhibitor. Compositions of a combination of an AT$_1$ specific Angiotensin II antagonist and an Angiotensin II agonist are also described. The compositions are useful for treating bladder dysfunction.

28 Claims, 11 Drawing Sheets

OTHER PUBLICATIONS

Kristian Waldeck, et al., "Characterization of Angiotensin II Formation in Human Isolated Bladder by Selective Inhibitors of ACE and Human Chymase: A Functional and Biochemical Study," British Journal of Pharmacology (1997), vol. 121, pp. 1081–1086.

Katarina Persson, et al., "Angiotensin II and Bladder Obstruction in the Rat: Influence on Hypertrophic Growth and Contractility," Am. J. Physiol. (1996), vol. 271, pp. R1186–R1192.

Venegas, J., et al., "Assessment and modeling . . . ", *Modeling in Physiology,* H2109–H2123.

Comiter, C., et al., "Urodynamic Risk Factors . . . ", *J. of Urology,* (1997), 158:181–184.

Braley, et al., "The Effects of Extra . . . ", Biochem. and Biophys. Res. Com., (1984), 123:2:810–815.

Price, et al., "Renin System Autonomy . . . ", 29th Annual Meeting, (1996), Abstract.

Price, et al., "The Paradox of the . . . ", 29th Annual Meeting, (1996), Abstract.

Price, et al., "Renal Perfusion is . . . ", 31st Annual Meeting, (1998), Abstract.

Persson, K., "Angiotensin II and Bladder . . . ", 1996, Abstract, *Amer J. Physiol,* 271:5:1–2, R1186–R1192.

Klinge, E., et al., "Comparative Study of Some Isolated Mammalian Smooth Muscle Effectors of Penile Erection", *Acta, Physiol, Scand,* 1997, 100:354–367.

Andersson, K. et al., "Characterization of Immunoreactive Arginine Vasopressin (AVP) in and Effects of on Isolated Human Penile Erectile Tissues", *The Journal of Urology.,* 1987, 137:1278–1282.

Croog, S., et al., "Sexual Symptoms in Hypertensive Patient", *Arch. Intern. Med.,* 1998, 148:788–794.

Clark, J., "A Possible Role of Angiotensin II in the Regulation of Male Sexual Behavior in Rats". *Physiology and Behavior,* 1988, 45:221–246.

Suzuki, H., et al., "Effects of First–Line Antihypertensive Agents on Sexual Function and Sex Hormones". *Journal of Hypertension,* 1988, 6(suppl 4): S649–S651.

Walley, T., et al., Adverse Effects of Captopril in Hospital Outpatients with Hypertension:, *Post Grad Med Journal,* 1990, 66:106–109.

Vickers, M., et al., "Angiotensin Production by Human Corporal Cavernosal Tissue". *The Journal of Urology,* 1992, 147:4, No. 100.

Haidle, G., et al., "Guidelines for Drug Treatment of Male Infertility". *Drugs,* 1:160–68.

Testa, M., et al., "Quality of Life and Antihypertensive Therapy in Men—A Comparison of Captopril with Enalapril". *The New England Journal of Medicine,* 1993, 328:907–913.

Goldstein, I., et al., "Impotence". 62nd Annual Meeting Program of the New England Section, American Urological Association, Inc—Session II, 1993, pp. 64–65.

Joubert, P., et al., "The Effects of papervine, Prostaglandin E–1, and Phenylephrine on the Pulsatile Angiotensin II Secretion by Human Corporal Cavernosal Tissue", *Journal of Urology,* 1993 149:4:245A. No. 125.

Lopes–Martins, R., "Pharmacological Characterization of Rabbit Corpus Cavernosum Relaxation Mediated by the Tissue Kallikrein–kinin System", *BB J. Pharmacol,* 1994, 113:81–86.

Prisant, L.M., et al., "Sexual Dysfunction with Antihypertensive Drugs". *Arch Intern Med,* 1994, 154:730–736.

Kifor, I., et al., "Tissue Angiotensin II and Impotence", The Endocrine Society 1995 Abstract Form, Jan. 1995.

Andersson, K., et al., "Characterization of Immunoreactive . . . ", *J. of Urology,* 1987, 137:1278–1282.

\* cited by examiner

COMPOSITIONS AND METHODS FOR TREATING BLADDER DYSFUNCTION

This application claims benefit of provisional applications Ser. No. 60/04,874, filed Apr. 11, 1997, also Ser. No. 60/04,875, filed Apr. 11, 1997.

BACKGROUND OF THE INVENTION

Bladder function is traditionally believed to be regulated, under neuromuscular control, through functional interrelationships between neural, muscular, and connective tissue components of the bladder. Dockray, GH..; Gut Peptides: *Biochemistry and Physiology,* Raven Press, New York, N.Y. (1994); p. 1–11, 423–445. The basic cytological aspects of bladder smooth muscle are similar to those of other visceral muscles. The detrusor muscle is composed of an integrated unit of interconnected smooth muscle bundles including on the ventral face of the bladder a large longitudinal muscle, a dorsal sheet-like component of circular musculature, and a mesh structure on the lateral portion of the bladder. Collagen fibrils, microfilaments and small elastic fibers are positioned between muscle cells and beneath the epithelium and serosa.

Bladder dysfunction is caused by abnormal functioning of the bladder tissue, resulting in symptoms such as dysuria, frequency and urgency, incontinence, enuresis or complete loss of function. Dysuria is a form of bladder dysfunction associated with pain or burning sensation during urination and urinary frequency. It often leads to a sense of bladder fullness resulting in frequent urination and can be caused by infection, radiation, chemicals, foreign bodies, (catheters and stones), and infiltration of the muscles by tumors of the bladder or from adjacent organs. Incontinence which is the inability to retain urine in the bladder can result from neurological or mechanical disorders of the system that controls normal micturition such as detrusor instability, stress incontinence and mechanical incontinence. Detrusor instability is a condition in which the bladder undergoes frequent and uncontrollable contractions that cause incontinence as a result of damaged neural pathways. Enuresis is an involuntary passage or urine at night or during sleep.

Bladder dysfunction such as incontinence is a major source of morbidity among the elderly, affecting more than 10 million Americans. Management of urinary incontinence accounts for more that 15% of nursing home budgets as a cost of 8 billion dollars annually.

A variety of diseases and injuries can contribute to or cause the development of bladder dysfunction. For example, benign prostatic hyperplasia (BPH), a common disorder occurring in adult men, often produces bladder outlet obstruction and bladder hypertrophy. The percentage of adult men with histological evidence of BPH increases every year after the fourth decade, such that 80% of men in their eighth decade have BPH.

Detrusor instability which is associated with uninhibited contraction of the bladder smooth muscle is a common cause of bladder dysfunction. Nearly two thirds of patients with bladder outlet obstruction have detrusor instability. Even after the removal of the obstruction detrusor instability persists in one-third of the patients. In addition to obstruction-induced forms, detrusor instability is associated with radiation cystitis, interstitial cystitis, bladder tumors, bladder stones, and is commonly found in elderly women who are otherwise free of obstruction of detrusor hypertrophy. A significant proportion of these patients do not respond to currently available pharmacologic agents or are unable to tolerate the side-effects of these medications.

The molecular pathophysiology of obstruction-induced bladder dysfunction is uncertain. Kitada et al., *J. Urology,* (1989); v, 141 p.166–169. However, in partial outlet obstruction produced in adult animals, the anatomical, histological, cellular and molecular changes impair both storage and emptying. In the early phase of the obstruction, smooth muscle hypertrophy permits an increase in detrusor contractility. As obstruction persists, increasing amounts of extracellular matrix proteins leads to a decreased compliance and decreased emptying. It is postulated that obstruction induces a phenotypic modulation in the smooth muscle cells which initially alters contractility of the cell, and then ultimately affects the expression of extracellular matrix proteins. *Lin, VK, Muscle, Matrix, and Bladder Function,* Plenum Press, New York, N.Y. (1995); p.65–74. In the hypertrophied bladder, the smooth muscle cells and the smooth muscle bundles are enlarged and collagen fibril bundles are larger and longer. The degree of hypertrophy is apparently similar in all smooth muscle cells within a bundle and can be associated with detrusor instability. Mostwin et al., *Muscle, Matrix, and Bladder Function,* Plenum Press, New York, N.Y. (1995); p.21–28. In a guinea pig model, partial outlet obstruction produced by a jeweler's ring placed around the urethra of immature animals caused a slow obstruction without acute distension, ischemia and other lesions. The bladder responded with an increased smooth muscle mass attributed to muscular hyperplasia. The collagen content of the bladder was proportional to the muscle mass, and no significant decrease in nerves containing acetylcholine was observed. Levin et al., *Muscle, Matrix, and Bladder Function,* Plenum Press, New York, N.Y. (1995); p. 7–19. With increasing bladder weight, urodynamic abnormalities appeared, such as significantly higher voiding pressures, unstable contractions similar to those seen in humans, and loss of compliance. The maximum bladder weight gain, i.e. 3 fold greater than the control value, was associated with a loss of contractility and overflow incontinence. The velocity of muscle contraction decreased as the weight increased. Mostwin et al., *Muscle, Matrix, and Bladder Function,* Plenum Press, New York, N.Y. (1995); p.21–28. The decreased active force of hypertrophic bladder muscle correlated well with the decreased myosin concentration. An alternative explanation could be the altered metabolic supply of ATP. Uvelius, B et al., *Muscle, Matrix, and Bladder Function,* Plenum Press, New York, N.Y. (1995); p.29–39. The level of nerve growth factor (NGF) and the mRNA for NGF was higher in the obstructed bladder than in controls. Depletion of intracellular thapsigargin sensitive $Ca^{++}$ stores blocks basal and stretch induced NGF production by cultured bladder smooth muscle cells. Protein kinase C (PKC) and tyrosine kinase also played an important role in stretch induced NGF production. Alterations in energetics, innervation, spontaneous contractile activity, and the accumulation of extracellular matrix proteins in hypertrophied bladder may contribute to an altered contractile force development and to the reduced ability of the bladder to empty. *Muscle, Matrix, and Bladder Function,* Plenum Press, New York, N.Y. (1995); p. 7–19, 29–40, 55–64.

Neurologic injury can also dramatically effect bladder function. In the United States 8,000 to 10,000 new cases of spinal cord injury are reported each year. Bladder dysfunction characterized by detrusor hyperreflexia and hypertrophy are common in patients with traumatic supra sacral spinal cord injury. These patients are typically incontinent, depending on the completeness of the lesion and the degree of external sphincter coordination. Maintaining continence in these patients can be difficult and often requires drastic procedures that decrease outlet resistance and completely suppress the bladder (external sphincterotomy with administration of anticholinergic agents) to preserve upper tract function. Many non-traumatic spinal cord diseases are also associated with detrusor hyperreflexia. These diseases include multiple sclerosis, amyotrophic lateral sclerosis, cervical spondylosis, epidural and meningeal tumors, syringomyelia, vascular malformations and radiation myelopathy. Detrusor hyperreflexia is also one of the most common consequences of cerebrovascular accidents, Parkinson's disease and Alzheimer's disease.

Nearly 50% of diabetics, which account for more than 2.5% of the American population, have some degree of bladder dysfunction. Bladder dysfunction in diabetics is caused by a variety of bladder abnormalities such as detrusor areflexia and detrusor hyperreflexia.

Significant bladder dysfunction can also occur as a result of pelvic plexus injury or abdomino-perineal resections. In these conditions, the bladder is characterized by hypocontractility and poor compliance due to a combination of sympathetic and parasympathetic injuries.

Children with congenital urethral obstruction have significant bladder dysfunction, contributing to urinary incontinence. The bladder abnormalities associated with bladder dysfunction in these children include detrusor instability, myogenic failure and poor bladder compliance. Bladder dysfunction often persists in these patients even after successful relief of the primary obstruction. Preservation of upper tract function depends on successful treatment of the bladder dysfunction.

Several therapies have been developed and are currently being used to treat bladder dysfunction. Therapies for detrusor instability include treatment with anticholinergic agents alone or in combination with musculotropic relaxants and local anesthetics such as oxybutynin and flavoxate. A significant proportion of patients with detrusor instability, however, do not respond to these agents. Anticholinergic agents are also associated with several side effects, including dry mouth, blurred vision, drowsiness and constipation. Other therapeutics which are sometimes used to treat detrusor instability include prostaglandin inhibitors, tricylelic antidepressants, beta-adrenergic agonists and alpha-adrenergic antagonists. There are no pharmacologic agents currently used to treat detrusor hypertrophy. Surgical procedures, such as removal of detrusor obstruction and external sphincterotomy, are often necessary for the treatment of bladder dysfunction.

It would be desirable to have a therapy that could be administered systemically and that could avoid the foregoing drawbacks.

SUMMARY OF THE INVENTION

The invention in one aspect is a method for treating bladder dysfunction by administering a renin-angiotensin system inhibitor to a subject having bladder dysfunction. The invention is based on the finding that, similar to the vascular tissue, the bladder smooth muscle produces and secretes an important modulator of bladder contraction, Angiotensin II. It was found according to the present invention that bladder smooth muscle produces and secretes Angiotensin II through the regulated secretory pathway (RSP) and that such locally produced Angiotensin II, in part, mediates muscarinic and adrenergic regulation of bladder tone and contractility. It was also discovered that Angiotensin II functions as a growth factor which modulates proliferation and hypertrophy of bladder smooth muscle cells and stimulates the production of extracellular matrix proteins. These findings indicate that locally produced Angiotensin II is involved in the regulation of cellular and tissue events leading to bladder hypertrophy and remodeling. An overproduction of Angiotensin II will initiate and maintain bladder hypertrophy and remodeling, while suppressing Angiotensin II production prevents and reverses this process. Therefore, inhibitors of Angiotensin II production, such as the renin-angiotensin II system inhibitors can prevent and reverse bladder hypertrophy and remodeling associated with bladder dysfunction.

Although previous in vitro studies demonstrated that Angiotensin II was capable of stimulating smooth muscle contraction in isolated bladder tissue, prior to the unexpected findings of the invention compounds which inhibit the production or activity of Angiotensin II were never believed to be potential therapeutics for the treatment of bladder dysfunction. Compounds which inhibit Angiotensin II, such as the renin-angiotensin system inhibitors have never been used to treat bladder dysfunction for a variety of reasons. One reason is that until the present invention it was not known that Angiotensin II was the physiological modulator of bladder smooth muscle contractility. Although it had previously been demonstrated that Angiotensin II inhibits smooth muscle contraction in vitro, it was not known that enough Angiotensin II was present in the local region of the bladder smooth muscle to actually mediated those effects in vivo. The present invention reveals that Angiotensin II is produced locally in the bladder in high concentrations. It was known that systemic Angiotensin II was present in the blood but those levels were not high enough to actually be involved in modulating contraction of bladder smooth muscle. So as a result no one suspected that Angiotensin II could be involved in mediating smooth muscle contraction in vivo. If Angiotensin II was not mediating smooth muscle contraction then there was no reason to suspect that inhibitors of Angiotensin II would inhibit smooth muscle contraction.

The invention in one aspect relates to a method for treating bladder dysfunction in a subject by administering to a subject exhibiting symptoms of bladder dysfunction a renin-angiotensin system inhibitor in an amount effective to decrease symptoms of bladder dysfunction. An effective amount of a renin-angiotensin system inhibitor is one which modifies systemic blood pressure by less than 10% within one day of administration. In one embodiment the renin-angiotensin system is an Angiotensin II antagonist. In one embodiment the Angiotensin II antagonist is losartan. The effective amount of the renin-angiotensin system inhibitor can be low enough whereby systemic blood pressure is lowered within one day of administration by even less than 5%, and in particular so low as to cause no measurable lowering of systemic blood pressure (i.e., no change in systemic blood pressure acutely). In one embodiment the renin-angiotensin system is administered orally. According to another embodiment the renin-angiotensin system inhibitor is administered by a sustained release implant.

In another embodiment the renin-angiotensin system inhibitor is an ACE inhibitor. In another embodiment the ACE inhibitor is selected from the group consisting of acylmercapto and mercaptoalkanoyl prolines, carboxyalkyl dipeptides, carboxyalkyl dipeptides mimics, and phosphinylalkanoyl prolines. Preferably the ACE inhibitor is selected from the group consisting of enalapril and captopril.

In yet another embodiment the renin-angiotensin system inhibitor is a renin inhibitor. In another embodiment the renin inhibitor is selected from the group consisting of a peptide, an amino acid, and an anti-renin antibody.

In another aspect the invention is a method for treating bladder hypertrophy and remodeling in a subject. The method includes the step of administering to a subject having bladder hypertrophy and remodeling a renin-angiotensin system inhibitor in an amount effective to reduce bladder hypertrophy and remodeling, and wherein the amount is one which modifies acutely systemic blood pressure of the subject by less than 10%. In one embodiment the renin-angiotensin system is an Angiotensin II antagonist. In one embodiment the Angiotensin II antagonist is losartan. The effective amount of the renin-angiotensin system inhibitor can be low enough whereby systemic blood pressure is lowered within one day of administration by even less than 5%, and in particular so low as to cause no measurable lowering of systemic blood pressure (i.e., no change in systemic blood pressure acutely). In one embodiment the renin-angiotensin system is administered orally. According to another embodiment the renin-angiotensin system inhibitor is administered by a sustained release implant. In another embodiment the renin-angiotensin system inhibitor is an ACE inhibitor.

In another embodiment the ACE inhibitor is selected from the group consisting of acylmercapto and mercaptoalkanoyl prolines, carboxyalkyl dipeptides, carboxyalkyl dipeptides mimics, and phosphinylalkanoyl prolines. Preferably the ACE inhibitor is selected from the group consisting of enalapril and captopril.

In yet another embodiment the renin-angiotensin system inhibitor is a renin inhibitor. In another embodiment the renin inhibitor is selected from the group consisting of a peptide, an amino acid, and an anti-renin antibody.

In another aspect the invention is a method for preventing bladder dysfunction in a subject. The method includes the step of administering to a subject at risk of developing bladder dysfunction a renin-angiotensin system inhibitor in an amount effective to prevent bladder dysfunction, and wherein the amount is one which modifies acutely systemic blood pressure of the subject by less than 10%. In one embodiment the renin-angiotensin system is an Angiotensin II antagonist. In one embodiment the Angiotensin II antagonist is losartan. The effective amount of the renin-angiotensin system inhibitor can be low enough whereby systemic blood pressure is lowered within one day of administration by even less than 5%, and in particular so low as to cause no measurable lowering of systemic blood pressure (i.e., no change in systemic blood pressure acutely). In one embodiment the renin-angiotensin system is administered orally. According to another embodiment the renin-angiotensin system inhibitor is administered by a sustained release implant. In another embodiment the renin-angiotensin system inhibitor is an ACE inhibitor.

In another embodiment the ACE inhibitor is selected from the group consisting of acylmercapto and mercaptoalkanoyl prolines, carboxyalkyl dipeptides, carboxyalkyl dipeptides mimics, and phosphinylalkanoyl prolines. Preferably the ACE inhibitor is selected from the group consisting of enalapril and captopril.

In yet another embodiment the renin-angiotensin system inhibitor is a renin inhibitor. In another embodiment the renin inhibitor is selected from the group consisting of a peptide, an amino acid, and an anti-renin antibody.

The invention also involves the surprising finding that bladder dysfunction can be treated by the administration of a combination of an $AT_1$ specific Angiotensin II antagonist and an Angiotensin II agonist. As described herein Applicants have discovered that Angiotensin II antagonists are useful for treating bladder dysfunction, hypertrophy and remodeling by inhibiting the contraction of bladder smooth muscle. Prior to the present invention it was not known that Angiotensin II agonists would potentiate the activity of $AT_1$ specific Angiotensin II antagonists when administered in conjunction with $AT_1$ specific Angiotensin II antagonists. This was surprising because agonists generally have the opposite effect of antagonists.

The invention in another aspect is a method for treating bladder dysfunction. The method involves the step of administering to a subject exhibiting symptoms of bladder dysfunction, an $AT_1$ specific Angiotensin II antagonist and an Angiotensin II agonist in an amount effective to decrease the symptoms of bladder dysfunction.

In another aspect the invention is a method for reducing the risk of acquiring bladder dysfunction. The method involves the step of administering to a subject at risk of developing bladder dysfunction, an $AT_1$ specific Angiotensin II antagonist and an Angiotensin II agonist in an amount effective to reduce the risk of acquiring bladder dysfunction.

In another aspect the invention is a method for treating bladder hypertrophy and remodeling. The method involves the step of administering to a subject having bladder hypertrophy and remodeling, an $AT_1$ specific Angiotensin II antagonist and an Angiotensin II agonist in an amount effective to reduce bladder hypertrophy and remodeling.

According to another aspect of the invention a pharmaceutical composition is provided. The pharmaceutical composition includes an $AT_1$ specific Angiotensin II antagonist, an Angiotensin II agonist, and a pharmaceutically acceptable carrier. The $AT_1$ specific Angiotensin II antagonist and the Angiotensin II agonist are present in an effective amount for treating bladder dysfunction.

The invention is useful, inter alia, in some embodiments in subjects who are otherwise free of indications calling for treatment with a combination of $AT_1$ specific Angiotensin II antagonist and Angiotensin II agonist and in other embodiments in subjects who are otherwise free of indications for renin-angiotensin system inhibition treatment.

Each of the limitations of the invention can encompass various embodiments of the invention. It is, therefore, anticipated that each of the limitations of the invention involving any one element or combinations of elements can be included in each method.

DETAILED DESCRIPTION OF THE INVENTION

Figure 1:
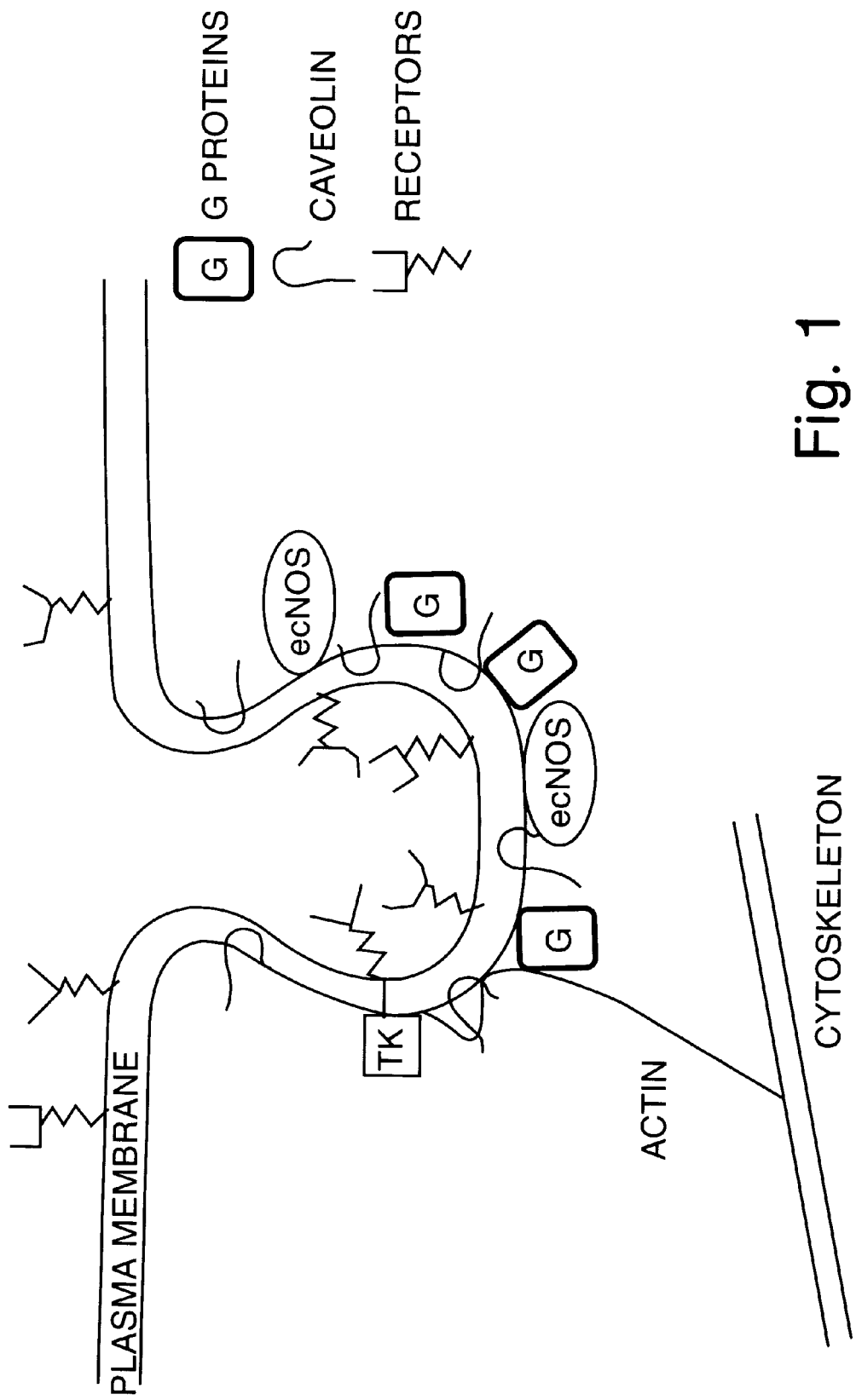
FIG. 1 is a schematic diagram showing several of the important receptors of the caveolae of bladder tissue.

Surprisingly, it has been discovered that treatment of subjects with a renin-angiotensin system inhibitor prevents and reverses bladder hypertrophy and remodeling associated with bladder dysfunction in subjects having bladder dysfunction. It was also discovered according to the invention that renin-Angiotensin II system inhibitors can be administered systemically in a dosage which improves bladder function by reducing bladder hypertrophy and remodeling but which does not affect systemic blood pressure by more than 10% avoiding the side effects caused by changes in the blood pressure. Inhibitors of the renin-angiotensin system are antihypertensive agents, and although both vascular and bladder smooth muscle are contracted by Angiotensin II, this peptide was not considered an important regulator of bladder function prior to the present invention.

The lack of effective medication for the prevention and treatment of bladder instability and hypertrophy reflects not only an inadequate understanding of the mechanisms involved in the development of bladder instability, but also an incomplete understanding of the normal regulation of bladder smooth muscle tone. The traditional concept of neuromuscular regulation of bladder function describes the functional interrelationships between neural, muscular and connective tissue components of the bladder. The findings of the present invention have elucidated the mechanisms involved in the development of bladder instability as well as the mechanisms involved in normal bladder smooth muscle tone providing insight into new therapeutic methods of treating bladder dysfunction. These findings demonstrate that bladder smooth muscle produces and secretes Angiotensin II and releases nitric oxide (NO), suggesting that Angiotensin II and NO produced by bladder smooth muscle cells are involved in paracrine and/or autocrine regulation of bladder function, and affect both the immediate and the chronic, adaptive responses of bladder smooth muscle. Because these factors are involved in the local regulation of bladder smooth muscle contractility, compounds that modulate the local production and activity of Angiotensin II are useful for inhibiting the contraction of bladder smooth muscle.

Although previous studies have indicated that muscarinic and adrenergic mediators play a role in smooth muscle cell contraction, prior to the invention the mechanism involved in this control was not known. The signal transduction pathways elicited by adrenergic and muscarinic receptors involve the mobilization of $Ca^{++}$ from $IP_3$ sensitive intracellular pools and increase $Ca^{++}$ influx. Therefore, agonist binding to muscarinic or α-adrenergic receptors increases the contractility of smooth muscle and possibly the secretion of regulatory peptides from smooth muscle cells via the RSP. This dual effect was determined by blocking the effect of Angiotensin II with specific receptor antagonists, such as losartan which significantly decreased the effect of muscarinic and adrenergic agonists on bladder smooth muscle contraction, suggesting that Angiotensin II mediates their effects.

As a growth factor and a secretagogue for other growth factors, Angiotensin II promotes proliferation, hypertrophy and the accumulation of extracellular matrix proteins. In the cardiovascular system, stretch-activated Angiotensin II release or overproduction of Angiotensin II promotes hypertrophy and cardiovascular remodeling. According to the present invention it was found that, similar to its role in the cardiovascular system, overproduction of locally produced Angiotensin II plays an important role in bladder hypertrophy and remodeling. As the bladder stretches growth factors are released from smooth muscle, suggesting the presence of stretch receptors in this tissue. In addition, Angiotensin II causes an increase in mitogen activated protein kinase (MAP kinase) activity in cultured bladder smooth muscle cells, indicating the presence of molecular mechanisms necessary to induce cell proliferation and/or hypertrophy.

The present invention relates to methods for treating bladder dysfunction by administering to a subject an effective amount of a renin-angiotensin system inhibitor to decrease or prevent the symptoms of bladder dysfunction and/or to reduce or prevent bladder hypertrophy and remodeling associated with bladder dysfunction. The renin-angiotensin inhibitor can be, for example, a renin-angiotensin system inhibitor that interferes with the activity of Angiotensin II or a renin-angiotensin system inhibitor that interferes with the production of Angiotensin II from angiotensinogen or angiotensin I. The renin-angiotensin system inhibitor can be administered in an effective dose which does not reduce the systemic blood pressure within one day of administration by more than 10%. It is preferred that the dose be low enough to cause an acute lowering of systemic blood pressure by no more than 5%.

The renin-angiotensin system inhibitor is administered in an effective amount. In one embodiment the effective amount is one that is sufficient to reduce or prevent bladder hypertrophy and remodeling associated with bladder dysfunction. In another embodiment the effective amount is one that is sufficient to reduce the symptoms of bladder dysfunction. In yet another embodiment the effective amount is one that is sufficient to prevent the symptoms of bladder dysfunction.

The invention also includes a composition and methods for treating bladder dysfunction by administering the composition. It was found according to the invention that a pharmaceutical combination of $AT_1$ specific Angiotensin II antagonists and Angiotensin II agonists causes smooth muscle relaxation in the bladder. The effect seen with the combination of drugs is greater than that seen with an Angiotensin II antagonist alone. The effect is surprising because agonists which generally have an opposite effect to that of antagonists usually do not potentiate the effect of an antagonist.

Although Applicants do not wish to be bound by a particular mechanism it is believed that Angiotensin II agonists potentiate the effect of $AT_1$ specific Angiotensin II antagonists by their interactions with different Angiotensin II receptors. Angiotensin II is known to specifically interact with at lest two cellular receptor subtypes $AT_1$ and $AT_2$.

The $AT_1$ receptor mediates the contractile effects of Angiotensin II and is involved in regulating the stimulation of regulatory peptide, growth factor and aldosterone secretion, cell proliferation, hypertrophy and secretion of extracellular matrix proteins. In the urinary bladder, the $AT_1$ receptor has a dominant role and when Angiotensin II is present, Angiotensin II interacts with the $AT_1$ receptor and causes smooth muscle contraction. Agonist binding to the G protein coupled $AT_1$ receptor activates PLC, and initiates a signal transduction pathway typical for G protein coupled receptors, with production of DAG and $IP_3$. The subsequent activation of PKC, mobilization of calcium from $IP_3$ sensitive intracellular stores, and the increased calcium influx through the L-type calcium channels promotes bladder smooth muscle contraction in a manner similar to Angiotensin II. Specific Angiotensin II receptor antagonists such as losartan suppress these effects.

The $AT_2$ receptors, however, are involved in mediation of smooth muscle relaxation and suppression of cell proliferation. The anti-growth effect of $AT_2$ receptors is mediated by inhibition of MAP kinase activity promoted by $AT_1$ receptors. When Angiotensin II or Angiotensin II agonists interact with $AT_2$ receptors the receptor is activated and promotes smooth muscle relaxation. Angiotensin II antagonists which interact with the $AT_2$ receptor inhibit the activation of the receptor and promote smooth muscle contraction.

The invention involves the finding that when both receptor subtypes are present in smooth muscle cells the balance between Angiotensin II, $AT_1$ specific Angiotensin II antagonists and Angiotensin II agonists can be manipulated to promote an enhanced stimulation of smooth muscle contraction through both sets of receptor subtypes. This is accomplished by using $AT_1$ specific Angiotensin II antagonists. When $AT_1$ specific Angiotensin II antagonists are added to smooth muscle cells expressing both $AT_1$ and $AT_2$ receptor subtypes, the $AT_1$ specific Angiotensin II antagonists specifically interact with the $AT_1$ receptors leaving the majority of the $AT_2$ receptors available. The interaction between the $AT_1$ specific Angiotensin II antagonists and the $AT_1$ receptors promotes smooth muscle relaxation. Under normal conditions the free Angiotensin II would interact with the available $AT_2$ receptors and not the $AT_1$ receptors because the $AT_1$ receptors are involved in the interaction with the $AT_1$ specific angiotensin II antagonist. The interaction of Angiotensin II with $AT_1$ receptors also promotes smooth muscle relaxation. When Angiotensin II agonists are added with the $AT_1$ specific Angiotensin II antagonists, the agonists specifically interact with the available $AT_2$ receptors, similar to Angiotensin II, resulting in the promotion of smooth muscle relaxation. The effect of Angiotensin II agonists is stronger than that of Angiotensin II. Therefore, by administering $AT_1$ specific Angiotensin II antagonists and Angiotensin II agonists together smooth muscle relaxation is stimulated through two pathways and is enhanced with respect to smooth muscle relaxation which occurs as a result of stimulation with $AT_1$ specific Angiotensin II antagonists alone.

In one embodiment, the present invention relates to a method for treating bladder dysfunction by administering to a subject a therapeutically effective dose of an $AT_1$ specific Angiotensin II antagonist and Angiotensin II agonist to decrease the symptoms of bladder dysfunction. The $AT_1$ specific Angiotensin II antagonist and Angiotensin II agonist can be administered in an effective amount which does not reduce the systemic blood pressure within one day of administration by more than 10%. It is preferred that the dose be low enough to cause an acute lowering of systemic blood pressure by no more than 5%.

The $AT_1$ specific Angiotensin II antagonist and Angiotensin II agonist are administered in effective amounts. In one embodiment the effective amount is one that is sufficient to prevent or reduce the risk of acquiring bladder hypertrophy and remodeling associated with bladder dysfunction. In another embodiment the effective amount is one that is sufficient to reduce the symptoms of bladder dysfunction. In yet another embodiment the effective amount is one that is sufficient to reduce the risk of acquiring the symptoms of bladder dysfunction.

An effective amount is that amount sufficient to produce a medically desirable result. Effective amounts will depend, of course, on the particular condition being treated; the severity of the condition, individual patient parameters including age, physical condition, size and weight, the duration of the treatment, the nature of the concurrent therapy (if any), the specific route of administration and like factors within the knowledge and expertise of the health practitioner. These factors are well known to those of ordinary skill in the art and can be addressed with no more than routine experimentation. For example, an effective amount for treating bladder dysfunction would be an amount sufficient to reduce the amount or activity of Angiotensin II in the bladder smooth muscle so as to lessen the contractile response of bladder smooth muscle to neural stimulation. Chronic administration of the renin-angiotensin system inhibitor of the invention will prevent an increased contractile response such as that associated with high sodium intake, suppression of NOS activity, and partial outlet obstruction. Thus, it will be understood that the renin-angiotensin system inhibitor of the invention can be used to treat bladder dysfunction prophylactically in subjects at risk of developing bladder dysfunction as well as in subjects exhibiting symptoms of bladder dysfunction and subjects having bladder hypertrophy and remodeling.

A "subject exhibiting symptoms of bladder dysfunction" is a subject who has a disorder involving abnormalities of bladder detrusor smooth muscle arising from overproduction of Angiotensin II or bladder hypertrophy and remodeling. Symptoms of bladder dysfunction include but are not limited to dysuria, frequency and urgency, incontinence, enuresis and complete loss of bladder function. The abnormalities of bladder smooth muscle may arise as a result of disease, chemicals, radiation, foreign bodies, (catheters and stones), and infiltration of the muscles by tumors of the bladder or may be simply due to advancement of age.

A "subject at risk of developing bladder dysfunction" is a subject who has a propensity of developing bladder dysfunction because of certain factors affecting the bladder of the subject. Factors which influence the development of bladder dysfunction include but are not limited to exposure to infectious agents, chemicals, radiation or foreign bodies, a predisposition to develop tumors of the bladder or adjacent organs and age. It is desirable to reduce the risk in these subjects of developing bladder dysfunction. Reducing the risk of bladder dysfunction includes a slowing of the progression towards bladder dysfunction or preventing the development of bladder dysfunction.

The term "subject" as used herein, is intended to mean humans, primates, horses, cows, swine, goats, sheep, dogs, and cats.

In one embodiment, the subjects treated by the methods of the present invention are otherwise free of indications for renin-angiotensin system inhibition treatment. By "free of indications for renin-angiotensin system inhibition treatment", it is meant that the subject does not have indications (e.g., symptoms or a clinical history) which, prior to the present invention, were known to involve treatment with a renin-angiotensin system inhibitor. For example, it previously has been shown that renin-angiotensin system inhibitors can be used to treat hypertension, congestive heart failure, myocardial infarction, erectile dysfunction and renal disease.

In another embodiment, the subjects treated by the methods of the present invention are otherwise free of indications for a combination of $AT_1$ specific Angiotensin II antagonist and Angiotensin II agonist. By "free of indications", it is meant that the subject does not have indications (e.g., symptoms or a clinical history) which, prior to the present invention, were treated with an $AT_1$ specific Angiotensin II antagonist and Angiotensin II agonist.

The renin-angiotensin system is involved in the regulation of hemodynamics and water and electrolyte balance. Factors that lower blood volume, renal perfusion pressure, or the concentration of $Na^+$ in plasma tend to activate the system, while factors that increase these parameters tend to suppress its function.

Angiotensin I and Angiotensin II are synthesized by the enzymatic renin-angiotensin pathway. The synthetic process is initiated when the enzyme renin acts on angiotensinogen, a pseudoglobulin in blood plasma, to produce the decapeptide angiotensin I. Angiotensin I is converted by angiotensin converting enzyme (ACE) to Angiotensin II (angiotensin-[1-8]octapeptide). The latter is an active pressor substance which has been implicated as a causative agent in several forms of hypertension in various mammalian species, e.g., humans.

Renin-angiotensin system inhibitors are compounds that act to interfere with the production of Angiotensin II from angiotensinogen or angiotensin I or interfere with the activity of Angiotensin II. Such inhibitors are well known to those of ordinary skill in the art and include compounds, such as renin and ACE inhibitors that act to inhibit the enzymes involved in the ultimate production of Angiotensin II, including renin and ACE. They also include compounds that interfere with the activity of Angiotensin II, once produced. Examples of classes of such compounds include antibodies (e.g., to renin), amino acids and analogs thereof (including those conjugated to larger molecules), peptides (including peptide analogs of angiotensin and angiotensin I), pro-renin related analogs, etc. Among the most potent and useful renin-angiotensin system inhibitors are renin inhibitors, ACE inhibitors, and Angiotensin II antagonists. In a preferred embodiment of the invention, the renin-angiotensin system inhibitors are renin inhibitors, ACE inhibitors, and Angiotensin II antagonists.

Angiotensin II antagonists are compounds which interfere with the activity of Angiotensin II by binding to Angiotensin II receptors and interfering with its activity. Angiotensin II antagonists are well known and include peptide compounds and non-peptide compounds. Most Angiotensin II antagonists are slightly modified congeners in which agonist activity is attenuated by replacement of phenylalanine in position 8 with some other amino acid; stability can be enhanced by other replacements that slow degeneration in vivo. Examples of Angiotensin II antagonists include: peptidic compounds (e.g., saralasin, [(San$^1$)(Val$^5$)(Ala$^8$)] angiotensin-(1–8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., *J Pharmacol. Exp. Ther.* 247(1), 1–7 (1988)); 4, 5, 6, 7-tetrahydro-1H-imidazo [4,5-c] pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to Angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(-1-naphthyl)-L-alanyl-(4, thiazolyl)-L-alanyl (35,45)-4-amino-3-hydroxy-5-cyclo-hexapentanoyl-N-hexylamide, Sankyo Company, Ltd., Tokyo, Japan); SKF108566 (E-alpha-2-[2-butyl-1-(carboxy phenyl) methyl] 1H-imidazole-5-yl[methylane]-2-thiophenepropanoic acid, Smith Kline Beecham Pharmaceuticals, Pa.); Losartan (DUP753/MK954, DuPont Merck Pharmaceutical Company); Remikirin (RO42-5892, F. Hoffman LaRoche AG); $A_2$ agonists (Marion Merrill Dow) and certain non-peptide heterocycles (G. D. Searle and Company).

Angiotensin converting enzyme, or ACE, is an enzyme which catalyzes the conversion of angiotensin I to Angiotensin II. ACE inhibitors include amino acids and derivatives thereof, peptides, including di and tri peptides and antibodies to ACE which intervene in the renin-angiotensin system by inhibiting the activity of ACE thereby reducing or eliminating the formation of pressor substance Angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

Renin inhibitors are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di and tri peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075,451); fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S.

Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437).

The renin inhibitors, ACE inhibitors, and Angiotensin II antagonists described herein are commercially available compounds, are derived from commercially available compounds or are synthesized de novo using routine chemical synthetic procedures known to those of ordinary skill in the art.

The renin-angiotensin inhibitors of the invention are administered in effective amounts. Generally, systemic doses of active compounds will be from about 0.01 milligrams/kg body weight per day to 10 milligrams/kg body weight per day. It is expected that oral doses in the range of 0.1 to 100 milligrams/kg body weight, in one or several administrations per day, will yield the desired results. In the event that the response in a subject is insufficient at such doses, even higher doses (or effective higher doses by a different, more localized delivery route) may be employed to the extent that patient tolerance permits. In the event that lower doses are sufficient to improve bladder function lower doses may be employed. Multiple doses per day are contemplated to achieve appropriate systemic levels of compounds. In one embodiment a maximal dose is administered first, followed by submaximal dosages. An effective amount is less than that which will have the effect of acutely modifying the systemic blood pressure greater than 10%. It preferably is so low so as to acutely modify systemic blood pressure by no more than 5% and can be even so low so as to have no measurable acute effect on systemic blood pressure.

The $AT_1$ specific Angiotensin II antagonist and Angiotensin II agonist of the invention also are administered in effective amounts for treating bladder dysfunction. Generally, systemic doses of active compounds will be from about 0.01 milligrams/kg body weight per day to 10 milligrams/kg body weight per day. It is expected that oral doses in the range of 0.1 to 100 milligrams/kg body weight, in one or several administrations per day, will yield the desired results. In the event that the response in a subject is insufficient at such doses, even higher doses (or effective higher doses by a different, more localized delivery route) may be employed to the extent that patient tolerance permits. In the event that lower doses are sufficient to improve bladder function lower doses may be employed. Multiple doses per day are contemplated to achieve appropriate systemic levels of compounds. In one embodiment a maximal dose is administered first, followed by submaximal dosages. An effective amount is less than that which will have the effect of acutely modifying the systemic blood pressure greater than 10%. It preferably is so low so as to acutely modify systemic blood pressure by no more than 5% and can be even so low so as to have no measurable acute effect on systemic blood pressure.

The invention also includes pharmaceutical compositions. The pharmaceutical composition includes an $AT_1$ specific Angiotensin II antagonist, an Angiotensin II agonist, and a pharmaceutically acceptable carrier.

The $AT_1$ specific Angiotensin II antagonist and the Angiotensin II agonist preferably are present in the composition in equivalent molecular ratios. The term "equivalent molecular ratios" as used herein means that the active agents in the composition have substantially equivalent numbers of molecules. The ratio of the active agents is dependent on the molecular weight of the active agents rather than the actual weight of the active agents.

$AT_1$ specific Angiotensin II antagonists are compounds which interfere with the activity of Angiotensin II by binding to $AT_1$ Angiotensin II receptors and interfering with its activity. $AT_1$ specific Angiotensin II antagonists are well known and include peptide compounds and nonpeptide compounds. Most $AT_1$ specific Angiotensin II antagonists are slightly modified congeners in which agonist activity is attenuated by replacement of phenylalanine in position 8 with some other amino acid; stability can be enhanced by other replacements that slow degeneration in vivo. Examples of $AT_1$ specific Angiotensin II antagonists include but are not limited to: Losartan (DUP753/MK954, DuPont Merck Pharmaceutical Company, U.S. Pat. No. 5,138,069 and EPO 0,253,310 (published Jan. 20, 1988) and EPO 0,324,377 (published Jul. 19, 1989); non-peptide Angiotensin II receptor antagonists (U.S. Pat. No. 5,264,581); polymorphic forms of losartan (U.S. Pat. No. 5,608,075)

$AT_1$ specific Angiotensin II antagonists of the invention are those which specifically interact with the $AT_1$ receptor subtype. They are well known in the art. Whether an angiotensin II antagonist specifically interacts with $AT_1$ can be determined using any of a number of art recognized assays. For example, whether an angiotensin II antagonist specifically interacts with $AT_1$ can be determined using the assay disclosed in U.S. Pat. No. 5,554,624, which is hereby incorporated by reference. Briefly, the assay involves the following:

A membrane fraction used in the assay is prepared from rat adrenal glands. The tissues are collected in 50 mM Tris-HCl buffer, pH 7.5, so that the concentration is 20% (w/v) and are homogenized at 1000×rpm. The homogenate is centrifuged at 1000 g for 10 min and the supernatant further centrifuged at 100,000 g for 1 h. The resulting membrane pellet is then resuspended in the above buffer at a concentration of 10 mg of protein/mL. 100 mu L aliquots of the membrane suspension can be stored frozen at $-70°$ C. until used.

Aliquots containing 15 mg of protein are incubated at 25° C. for 1 h in incubation buffer containing (final concentrations): NaCl (120 mM), $Mg_2$ (5 mM), 0.05% bovine serum albumin, and Tris (50 mM), adjusted to ph 7.5, with or without dithiothreitol (1 mM) to characterize whether drugs preferentially interact with $AT_1$ or $AT_2$ receptor subtypes. Incubation is initiated by the addition of 10 nM 3H-Angiotensin II. Total incubation volume is 250 mL. Nonspecific binding is measured by incubation in the presence of 0.1 mu M Sar<1>,Ile<8>-Angiotensin II. Test compounds are studied in the range of concentrations 10<-10>M-10<><5>M. Binding is terminated by rapid filtration using a Millipore Multiscreen device. Filters are washed three times with 250 mL of the corresponding buffer in the presence or absence of 1 mM dithiothreitol. Dry filters are placed into vials containing 3 mL of scintillation fluid and the radioactivity counted in a scintillation counter. The $IC_{50}$ value (concentration for 50% displacement of the specifically bound 3H-angiotensin II) is determined for each test compound.

The Angiotensin II agonists of the invention may specifically interact with both of the $AT_1$ and $AT_2$ receptor subtypes. Optionally the Angiotensin II agonist may specifically interact with the $AT_2$ receptor. Angiotensin II agonists include but are not limited to p-aminophenylalanine6 angiotensin II (Speth et al. *Biochem Biophys Res Commun* 169 (3), p. 997–1006 (1990)); guanosine 15 5'-O-(3-thiotriphosphate (Speth et al. *Biochem Biophys Res Commun* 169 (3), p. 997–1006 (1990)); (6-biotinylamido)hexanoyl-Angiotensin II (Bonnafous et al., *J. Recept Res.*, v. 8 (1–4), p. 295–309 (1988)); dinitrophenyl-aminohexanoyl-Angiotensin II (Bonnafous et al., *J. Recept Res.*, v. 8 (1–4), p. 295–309 (1988)); [Hfv5]Angiotensin II (Vine et al., *J. Med Chem*, v. 24 (9), p. 1043–1047 (1981)); agonist analogues of angiotensin II including [Des-Asp1]heptapeptide and [Sar1]-derivatives (Saltman et al., *Endocrinology*, v. 97, p. 275–282 (1975)); Angiotensin II, Asp-Arg-Val-Tyr-His-Pro-Phe and other agonists disclosed (Plucinska et al., *J. Med. Chem*, v. 36, p. 1902–1913 (1993)); and [Hcy3,5] Angiotensin II (Spear et al., *J. Med Chem*, v. 33, p. 1935–1940 (1990).

The $AT_1$ specific Angiotensin II antagonists and Angiotensin II agonists described herein are commercially available compounds, are derived from commercially available compounds or are synthesized de novo using routine chemical synthetic procedures known to those of ordinary skill in the art.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. As used herein, a renin-angiotensin system inhibitor means the compounds described above as well as salts thereof and a composition of an $AT_1$ specific Angiotensin II antagonist and Angiotensin II agonist means the compounds described above as well as salts thereof.

The renin-angiotensin system inhibitor or the $AT_1$ specific Angiotensin II antagonist and Angiotensin II agonist may be combined, optionally, with a pharmaceutically-acceptable carrier. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

Compositions suitable for parenteral administration conveniently comprise a sterile aqueous preparation of the renin-angiotensin system inhibitor or the $AT_1$ specific Angiotensin II antagonist and Angiotensin II agonist, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend of course, upon the particular drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule.

The pharmaceutical compositions may conveniently be presented in unit dosage form and may be prepared by any of the methods well-known in the art of pharmacy. All methods include the step of bringing the renin-angiotensin system inhibitor or the $AT_1$ specific Angiotensin II antagonist and Angiotensin II agonist into association with a carrier which constitutes one or more accessory ingredients. In general, the compositions are prepared by uniformly and intimately bringing the renin-angiotensin system inhibitor or the $AT_1$ specific Angiotensin II antagonist and Angiotensin II agonist into association with a liquid carrier, a finely divided solid carrier, or both, and then, if necessary, shaping the product.

Compositions suitable for oral administration may be presented as discrete units, such as capsules, tablets, lozenges, each containing a predetermined amount of the renin-angiotensin system inhibitor or the $AT_1$ specific Angiotensin II antagonist and Angiotensin II agonist. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the renin-angiotensin system inhibitor or the $AT_1$ specific Angiotensin II antagonist and Angiotensin II agonist described above, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the renin-angiotensin system inhibitor is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

As described above, many variations on these particular examples are possible and, therefore, the examples are merely illustrative and not limiting of the present invention.

EXAMPLES

Example 1: Bladder smooth muscle produces and secretes Angiotensin II via the regulated secretory pathway (RSP).

Introduction

Bladder function is regulated at the neuromuscular level by functional interrelationships between neural, muscular, and connective tissue components of the bladder. The experiments set forth below demonstrate that the neuromuscular regulation of bladder smooth muscle functions is complemented by the modulatory effects of autocrine and/or paracrine regulators such as angiotensin II and nitric oxide produced by endothelial type nitric oxide synthase (ecNOS) and bladder smooth muscle cells. Angiotensin II is secreted by bladder smooth muscle cells through the cytosolic calcium dependent RSP and is released in response to neural and paracrine stimulation. The data also demonstrate that angiotensin II and nitric oxide affect both the immediate and the chronic adaptive responses of bladder smooth muscle. An angiotensin II antagonist significantly decreased the effect of muscarinic and adrenergic agonists on bladder smooth muscle contraction indicting that Angiotensin II mediates their effects.

Angiotensin II, or NO, mediate in part the effects of neurotransmitters by paracrine or autocrine regulatory loops. In cardiomyocytes NO clearly modulates the calcium currents and myocyte contractions in response to muscarinic receptor activation. The data presented herein clearly indicate, that losartan, an Angiotensin II receptor antagonist, modulates the effects of muscarinic or adrenergic neurotransmitters on bladder smooth muscle.

The integration of neural and paracrine or autocrine regulation in a complex regulatory system is greatly enhanced by co-localization of the elements of this regulatory system in specific micro domains of the plasma membrane. In a variety of cells, including smooth muscle and endothelial cells, the cell surface is studded with small, flask-shaped membrane invagination called caveolae. The plasma membrane isolated from these invagination is enriched with cholesterol, other lipids and glycosylphosphatidylinositol (GPI) anchored membrane proteins. The caveolae function to concentrate small molecules, proteins, ions and, in particular, calcium in a sequestered space which can be transiently sealed off from the extracellular environment. These concentrated small molecules and ions are then translocated into the cell through channels or other transmembrane transport mechanisms (potocytosis). Another important feature of caveolae is the presence of palmitoylated G proteins, ecNOS, tyrosine kinase, Ras, raf, and a variety of receptors (Shown in FIG. 1). In contrast to the clathrin coated pits, the caveolae are not removed from the plasma membrane area. Receptors, G proteins, and the members of the src family of tyrosine kinases are linked to caveolin-3.

Figure 2A:
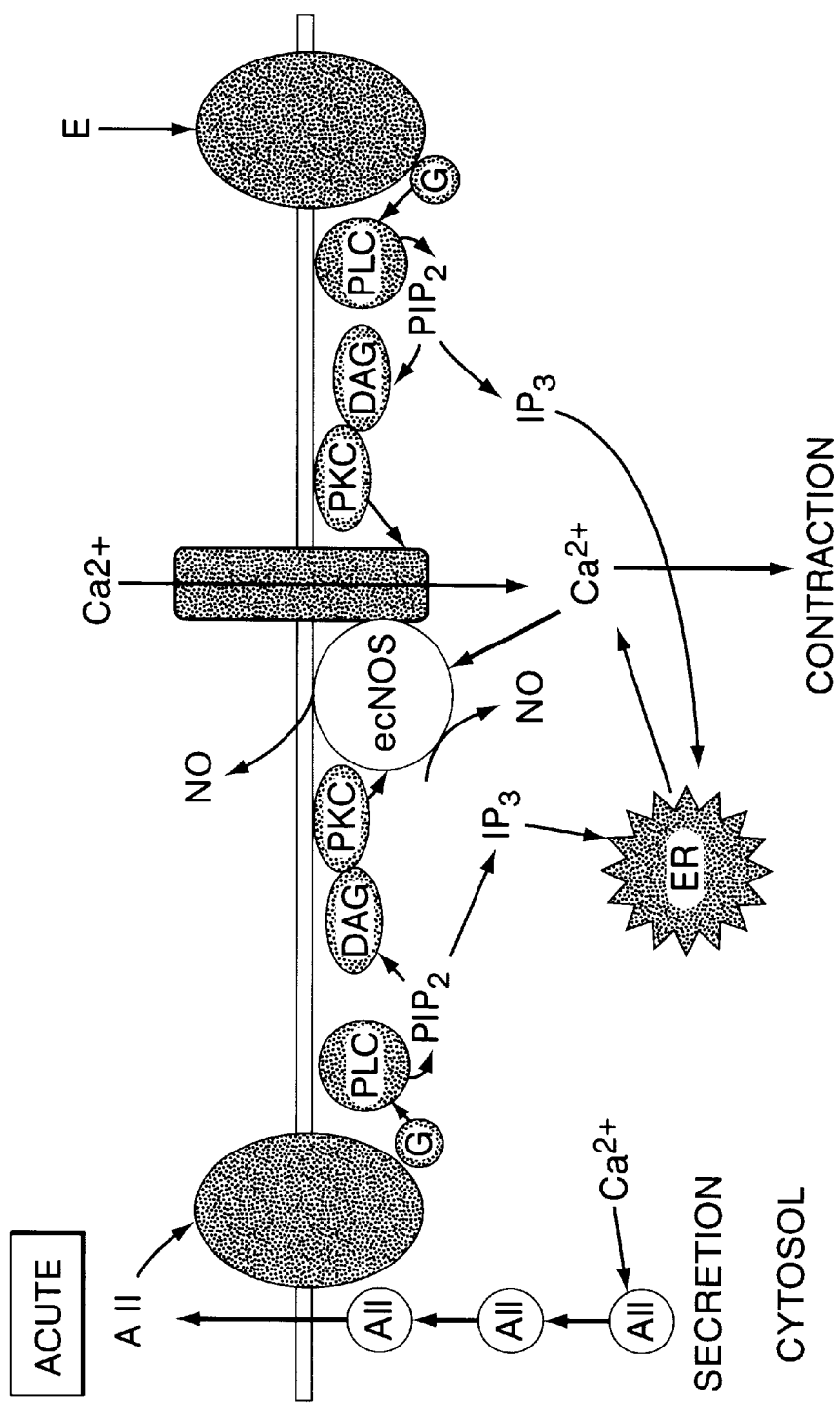
FIG. 2a and 2b are schematic diagrams depicting the regulatory interactions occurring between neurotransmitters, Angiotensin II and NO in the caveolae of bladder smooth muscle cells. Arrows with the double lines indicate default processes, arrows with the single line indicate activation, while arrows with the dashed line indicate inhibitory regulatory loops.
Figure 2B:
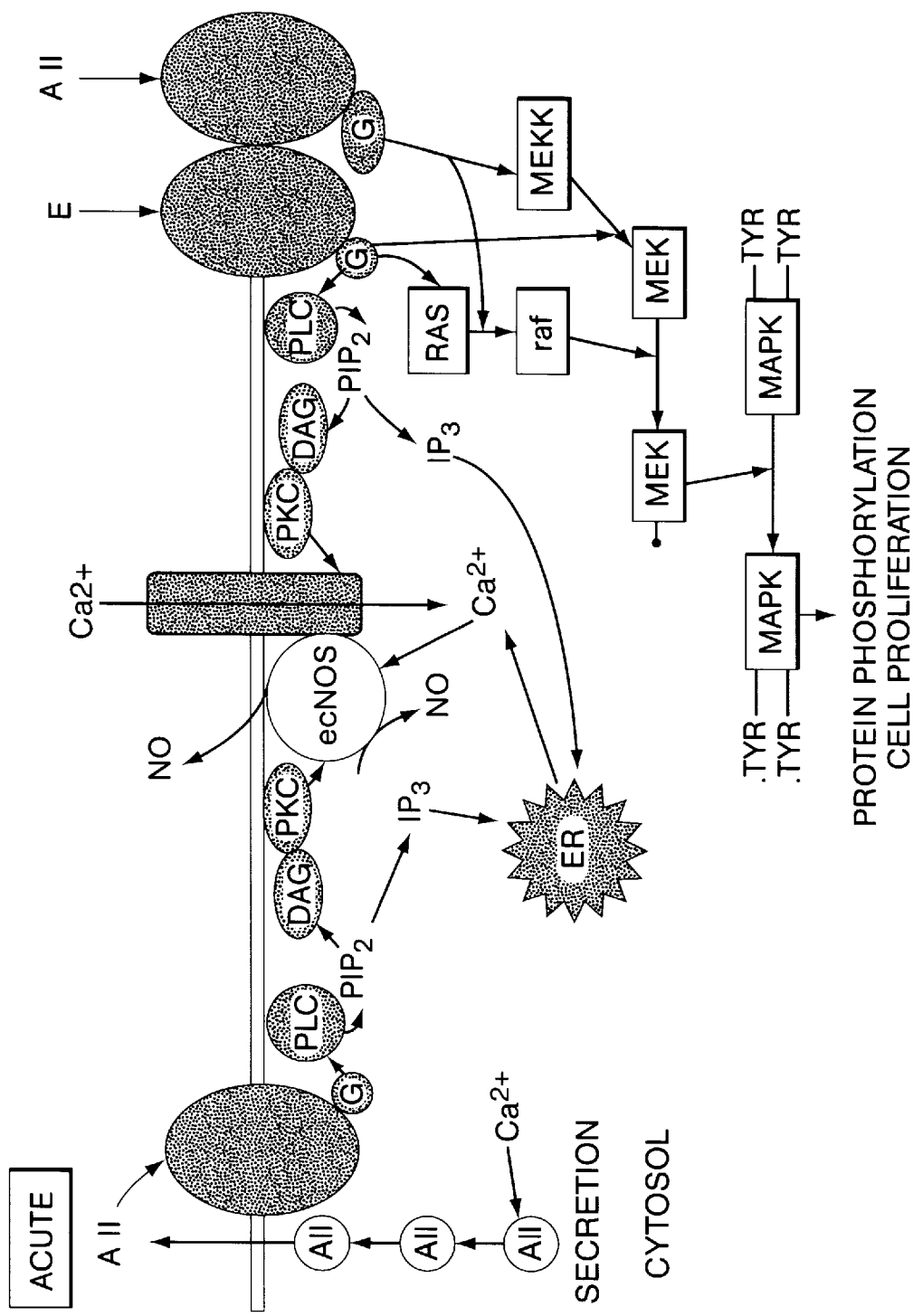

In FIGS. 2a and 2b the regulatory interactions between neurotransmitters, Angiotensin II and NO in the caveolae of bladder smooth muscle cells are presented. The arrows having double lines indicate default processes, the arrows having single lines indicate activation, while the arrows having dashed lines indicate inhibitory regulatory loops.

Adrenergic and muscarinic (not shown) receptors expressed in the bladder are G protein linked. Ligand binding to these receptors activates PLC, leading to diacylglycerol (DAG) and $IP_3$ production. Binding of DAG activates PKC, while $IP_3$ releases calcium from the endoplasmic reticulum (ER). The net result of the release of calcium from the ER, and the activation of PKC stimulates calcium influx from the extracellular space, producing high cytosolic calcium which induces smooth muscle contraction. Calcium influx increases secretion via the regulated secretory pathway (RSP), leading to release of Angiotensin II from smooth muscle cells. Angiotensin II released in the local area binds to its receptor in the caveolae. Secretion is initiated mainly by calcium influx via L-type channels that produce a high local cytosolic calcium level necessary to induce exocytosis. Therefore, the calcium channels and the site of exocytosis are in the same microdomain of the plasma membrane. The Angiotensin II is known to induce smooth muscle contraction and to increase the secretion of regulatory peptides and growth factors. High cytosolic calcium activates ecNOS and increases NO production. However, high cytosolic calcium activates several protein kinases that phosphorylate ecNOS. This phosphorylation decreases ecNOS activity and NO production. PKC activated by Angiotensin II has a similar effect. The simultaneous activation of constitutive NOS and the protein kinases leads to a short term activation of ecNOS and a quantum-like release of NO. NO decreases calcium influx, thus relaxes smooth muscle and suppresses secretion of regulatory peptides and growth factors.

Epinephrine, Angiotensin II, endothelin and growth factors activate a variety of signal transduction pathways. Activation of MAP kinase (or ERK) signal transduction pathway results in cell proliferation and hypertrophy. The major events initiated by epinephrine or Angiotensin II are similar. Agonist binding activates G protein complexes that activate Ras and raf and result in a complex cascade that lead to activated, phosphorylated MAP kinase. Phosphorylation of nuclear proteins initiate activation of various genes involved in cell proliferation. Ras and MAP kinase were identified in the caveolae, while agonist binding is associated with the translocation of Ras to the cytosol and raf from cytosol to the caveolae. The substrate molecules for MAP kinase are also translocated from the cytosol to the caveolae.

The role of Angiotensin II in mediating the acute effects of neurotransmitters (e.g. secretion and smooth muscle contraction) and the response of smooth muscle to stretch and mechanical overload (e.g. cell proliferation and hypertrophy) is complex. For example, Angiotensin II modulates TGF, production and secretion that increases collagen production. Angiotensin II receptor antagonists can interrupt regulatory loops initiated, supported and maintained by Angiotensin II. Decreasing Angiotensin II production with ACE inhibitors or limiting its effects with Angiotensin II receptor antagonists prevent and reverse the growth promoting effects of Angiotensin II produced locally.

The following experiments were designed to elucidate the complex mechanisms involved in bladder smooth muscle regulation. The data, as shown below, indicate that an Angiotensin II receptor antagonist suppresses spontaneous activity and contractions elicited by electric stimulation or carbachol indicating that Angiotensin II is an additional mediator of neural stimulation in the bladder. Thus, signal transduction subsequent to adrenergic receptor activation involves increasing cytosolic calcium levels, which increases Angiotensin II secretion. Angiotensin II released this way can mediate the effect of adrenergic neurotransmitters in a manner similar to that documented in vascular tissue.

Methods

Tissue and cell preparation. Rats were anesthetized by intraperitoneal injection of 0.25 ml of sodium pentobarbital. After 5 minutes, a surgical plane of anesthesia was verified by toe pinch. The abdominal cavity was opened and the bladder quickly removed. Bladder samples necessary to measure Angiotensin content or used for immunehistochemistry were wiped and instantly frozen in liquid nitrogen. Bladder samples assigned for superfusion, preparation of Angiotensin II secreting single cells, for in vitro studies or for primary cell cultures were placed immediately into ice cold Dulbecco modified Eagle's medium (DMEM) containing 0.1% protease free bovine serum albumin (BSA). Tissue samples assigned for single cell production, i.e. Angiotensin II secretion or cell culture, were cut in small pieces on an ice cool support, dispersed with collagenase D/dispase/DNase, and washed. A detailed description of these methods was previously published.

Immunohistochemistry. About 4–10 micron frozen sections were air dried for 5 minutes and fixed with cold (−20° C.) acetone for 10 minutes. The endogenous peroxidase was blocked using Dako peroxidase blocking reagent (Dako Corporation, Carpinteria, Calif.), and non-specific protein binding was suppressed by exposing the slices to Dako blocking solution for an hour. After washing, the slices were incubated for an hour with the first antibody, and after repeated washing with Dako washing solution the slices were incubated with the peroxidase labeled second antibody (Dako). Finally, after washing, the slices were incubated with a Dako AEC substrate system for 15 minutes, washed and mounted using mounting solution. Adjacent slices were used as controls. The controls were incubated with pre-immune serum of the same species as the first antibody, or the anti Angiotensin II antibody was saturated with synthetic Angiotensin II prior to application.

Chromatographic (HPLC) separation of angiotensin peptides. Frozen tissue or enzymatically dispersed cells were homogenized, extracted and the angiotensin peptides separated by HPLC as described previously.

Radioimmunoassay (RIA): The amount of individual angiotensin peptides within the HPLC fractions, or the amount of Angiotensin II in the superfusate were quantitated by RIA. A double antibody method was used as described previously.

Superfusion of enzymatically dispersed cells. Equal aliquots of collagenase dispersed rat bladder smooth muscle cells, about 2–3×10$^6$ cells, were superfused at 37° for 210 minutes as previously described.

Angiotensin II secretion by collagenase dispersed single cells. Bladder smooth muscle obtained from rats kept on normal, low or high sodium diet, or having experimental partial outlet obstruction were enzymatically dispersed. The single cells were incubated on Immobilon transfer membrane, and Angiotensin II secreted by smooth muscle cells were visualized and evaluated by a micro-western blot type assay previously published.

Results

The distribution of Angiotensin II within the bladder: The data revealed extensive staining for Angiotensin II in the rat bladder, urothelium, blood vessels and the bladder smooth muscle. Angiotensin II was localized to smooth muscle bundles, urothelium and cross sections of blood vessels. The uneven distribution pattern of Angiotensin II in bladder smooth muscle is reminiscent of the uneven endothelin distribution in smooth muscle bundles of the gastrointestinal system.

Losartan, an $AT_1$ receptor antagonist, had a significant impact on the spontaneous and EFS, carbachol and potassium induced contractions, supporting the physiological relevance of locally produced Angiotensin II. The data suggest that locally produced Angiotensin II are implicated in the regulation of bladder function. To further demonstrate that Angiotensin II plays a role experiments were performed to show that a) Angiotensin II is secreted "on demand", and b) that the secretion responds to neural and paracrine stimulation.

a) The "on demand" secretion of regulatory peptides is assisted by a constant overproduction and a regulated intracellular dissipation of the superfluous secretory granules that contain pre-formed peptides. This mechanism generates two Angiotensin peptide containing intracellular pools. 1) The secretory granule pool contains mostly Angiotensin II and a small amount of Angiotensin I. This pool is secreted. 2) The degradation of superfluous secretory granules within the lysosomal compartment by amino-, carboxy-, and endopeptidases generates a non-secreted second intracellular pool, containing bioactive Angiotensin I and Angiotensin II degradation products. The intracellular peptide degradation can be blocked by chloroquine, leading to an increased Angiotensin II secretion from a single pool. Chronic functional overload, i.e. stretch, resulting in hypertrophy, or dietary sodium intake, will also reduce lysosomal degradation of secretory granules, increasing Angiotensin II secretion and the ratio of Angiotensin II to the degradation products.

b) High cytosolic calcium promotes, while low cytosolic calcium suppresses secretion via the RSP. Therefore, neurotransmitters, neuropeptides and paracrine regulators that modulate cytosolic calcium levels by receptor or ion channel mediated pathways will modulate the secretion of Angiotensin II. Calcium influx through L-type calcium channels plays a special role in modulation of peptide secretion by endocrine and paracrine cells, and plays an important role in modulation of smooth muscle contraction. Therefore, modulation of L-type channel activity can particularly affect smooth muscle tone and Angiotensin II secretion by bladder smooth muscle cells. In addition to chemical stimulation, activation of stretch receptors can also increase cytosolic calcium. Since the secretion of nerve growth factor from the bladder is stretch mediated, we hypothesize that stretch may stimulate Angiotensin II secretion from bladder smooth muscle.

Example 2: Angiotensin produced by bladder smooth muscle in part mediates muscarinic and adrenergic regulation of bladder tone and contractility Results Spontaneous activity: Smooth muscle strips prepared from rat bladder exhibit significant spontaneous activity. Losartan ($10^{-5}$–$10^{-3}$M), an $AT_1$ receptor antagonist, decreased significantly both the amplitude and frequency of spontaneous contractions in a dose dependent manner. Since the effect of losartan is very specific, this observation demonstrates that the spontaneous contractions of bladder smooth muscle are caused by Angiotensin II release.

Electric field stimulation: Electric field stimulation (EFS) causes the release of mainly acetylcholine from the detrusor and mainly adrenergic neurotransmitters from bladder strips tissue of the bladder. Agonist binding to muscarinic receptors in bladder smooth muscle activate a signal transduction pathway which results in high cytosolic calcium. In addition to smooth muscle contraction, high cytosolic calcium promotes secretion via the regulated secretory pathway. The data which indicates that losartan ($10^{-3}$M) significantly decreased the contractions induced by EFS (10 volts, 5 msec, 1–64 Hz) in both the base and the dome reveals that the receptor mediated increase in cytosolic calcium increases Angiotensin II secretion from smooth muscles. Adrenergic neurotransmitters are powerful secretagogues of Angiotensin II in the vascular tissue.

Carbachol stimulation of bladder smooth muscle strips: The data reveals that Losartan significantly decreased the contractile effect of carbachol. Activation of muscarinic receptors in bladder smooth muscle increases cytosolic calcium, causes contraction and increases secretion by paracrine or autocrine cells. The observation that losartan ($10^{-3}$M) significantly decreased the contractile effect of carbachol ($10^{-8}$–$10^{-3}$M)) on bladder smooth muscle indicates that carbachol releases Angiotensin II. The contraction of bladder smooth muscle in response to carbachol has a large atropine resistant component. This atropine resistant component likely is the contraction elicited by Angiotensin II, secreted in response to carbachol.

Methoxamine stimulation of bladder smooth muscle strips: Methoxamine ($10^{-7}$–$10^{-3}$M) caused a contraction of the bladder strips prepared from the base. Losartan abolished this response. Adrenergic neurotransmitters increase the secretion of Angiotensin II from vascular tissue.

Figure 3:
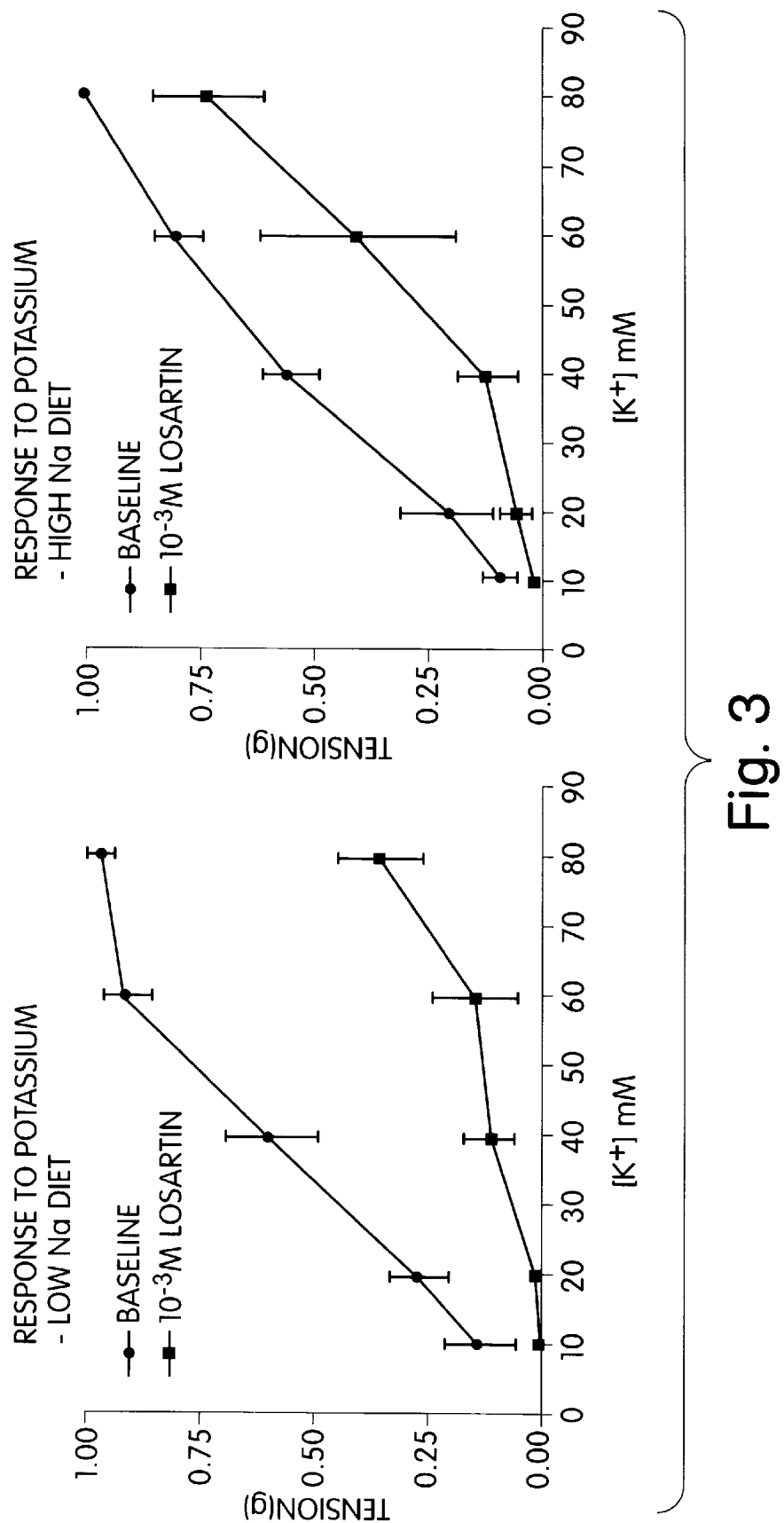
FIG. 3 is a graph which depicts the contractile effect of Lyosorption on bladder smooth muscle.

Extracellular potassium stimulation: Extracellular potassium in a range of concentrations of 3.5 mM–80 mM causes bladder smooth muscle contraction. The data indicate that losartan substantially decreased the contractile effect of extracellular potassium (See FIG. 3). This indicates that high extracellular potassium stimulates Angiotensin II release from bladder smooth muscle which complements the direct contractile effect of potassium. In fact, this mechanism has been shown in the vascular tissue, where losartan also decreased the contractile effect of extracellular potassium.

Analysis

In the bladder, similar to the heart, the contractile smooth muscle cells produce, secrete and release autocrine regulators, such as Angiotensin II and NO, that modulate their own function. In these cells both smooth muscle contraction and the production and release of autocrine regulators, i.e. Angiotensin II and NO, depend on cytosolic calcium levels. Muscarinic and/or adrenergic neurotransmitters increase cytosolic calcium levels by releasing calcium from intracellular pools and by promoting calcium influx and could simultaneously promote the contraction of bladder smooth muscle and increase the secretion of Angiotensin II. Angiotensin II mediates the effect of neurotransmitters by an autocrine regulatory loop. The existence of this dual effect is supported by the data presented herein, indicating that losartan, an Angiotensin II receptor antagonist, decreases the contractile effect of EFS, carbachol and methoxamine in bladder smooth muscle and similarly that adrenergic neurotransmitter mediated secretion is a major regulator of Angiotensin II secretion from vascular tissue.

The data of the invention indicate that ecNOS is a component of the caveolae in the bladder smooth muscle cells and mediates muscarinic receptor activity, indicating that the Angiotensin II receptor is another component of the caveolae. The co-localization of ecNOS, 10 muscarinic or adrenergic and Angiotensin II receptors in the caveolae enhances the modulation of the neurotransmitter's effects and the mutual regulation of the effects elicited by NO and Angiotensin II.

Since the effects of Angiotensin II and NO were dose dependent, the amount of Angiotensin II or NO released in response to stimulation has a great impact on the smooth muscle responsiveness. One of the most important physiologic regulators of Angiotensin II and NO production in various tissues and endocrine glands is the level of dietary sodium intake. Angiotensin II and NO production in the adrenal gland, kidneys and cardiovascular system, and hormone production by the central nervous system can be altered substantially by varying salt intake. The data indicate that dietary sodium intake had a significant impact on the responsiveness of bladder smooth muscle to carbachol and losartan exposure.

Example 3: Nitric oxide (NO) produced by bladder smooth muscle cells modulate muscarinic and adrenergic receptor activity.

Methods ecNOS in enzymatically dispersed single cells and cryosections: Collagenase dispersed cells were incubated on Immmobilon P transfer membrane as for Angiotensin II secretion. After incubation and removal of the media, blocking solution that contains 0.3% Triton×100 was applied for 60 minutes. Then the cells were incubated overnight with a monoclonal anti eNOS antibody in a dilution of 1:20 (Transduction Labs, Lexington, Ky.). After washing, a biotinylated second antibody was added for 4 hours, followed by streptavidin-alkaline phosphatase complex for 60 minutes. The substrate:NBT/BCIP, contains 1 mg/ml levamisole to inhibit endogenous alkaline phosphatase activity. A similar technique was applied to determine ecNOS distribution in cryosections. About 4–6 $\mu$m thick sections mounted on treated microscope slides were treated in a similar way as single cells.

NOS activity of collagenase dispersed single cells: Collagenase dispersed cells were incubated on Immobilon P transfer membrane as for Angiotensin II secretion. The cells were exposed to Angiotensin II ($10^{-7}$–$10^{-4}$M) or L-NAME ($10^{-4}$ M) for 60 minutes. After the experiments, the media was removed and the cells were fixed with 4% formaldehyde in PBS for 5 minutes. The cells were then incubated with 0.1%NADPH, 0.02% nitro-blue-tetrazolium (NBT) and 0.3% Triton X 100 at 37° C. for 30 minutes. The cell size and gray value of cells was determined with video image analysis. Cryosections obtained from bladder were mounted on microscope slides and treated as described for single cells.

Results

The distribution pattern of nitric oxide synthase in dog and rat bladder: The distribution patterns of ecNOS and brain NO synthase in the bladder were determined by immunohistochemical reaction using anti-ecNOS and anti-bcNOS monoclonal antibodies. The NOS activity was determined by diaphorase reaction performed in formaldehyde fixed cryosections. The bcNOS appeared in smooth muscle bundles and around blood vessels as a diffuse, granular structure. In contrast, the immunohistochemical reaction for ecNOS was positive in both the urothelium and smooth muscle. The intracellular staining was diffuse and weak, while the plasma membranes displayed a stronger reaction. This distribution pattern is consistent with the targeting of ecNOS to the membrane-bound caveolae. The distribution pattern of the imrnmunohistochemical reaction for ecNOS and diaphorase activity were similar. In the muscular layer, the diaphorase activity in various smooth muscle bundles was uneven, somewhat similar to the distribution pattern of Angiotensin II staining. In the urothelium, the intensity of diaphorase reaction was particularly high in the membrane fraction.

The distribution pattern of Caveolin-3: The immunohistochemical reaction supports a membrane-bound distribution pattern for caveolin-3, a marker protein of caveolae. In fact, the higher intensity of staining adjacent to the plasma membrane is consistent with the targeting of this protein to the caveolae.

Figure 4:
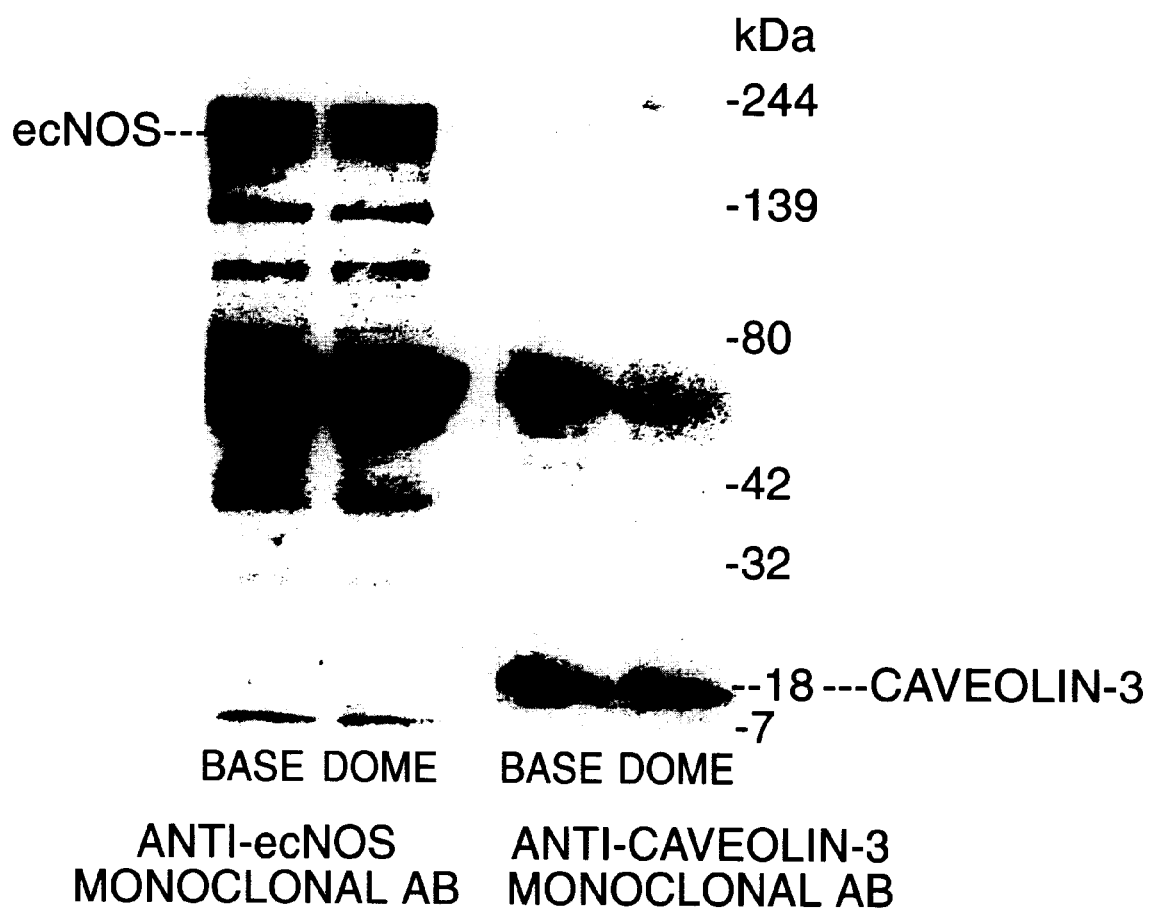
FIG. 4 is a Western blot of ecNOS and caveolin-3 in bladder smooth muscle. Separation and identification of ecNOS and caveolin-3 from primary cultures of rat bladder smooth muscle cells obtained from base and dome by SDS-PAGE (7.5%) and Western Blot. Both ecNOS and caveolin-3 were present in base and dome extracts. BioRad Kaleidoscope™ M.W. Markers are shown on the right.

Western blot analysis of ecNOS. caveolin-1 and caveolin-3 Confluent primary bladder smooth muscle cell cultures produced from bladder dome or base were homogenized, the proteins separated by SDS PAGE and immunoblotted on a transfer membrane. ecNOS was identified by a monoclonal antibody, while caveolin-1 and caveolin-3 were identified with polyclonal and monoclonal antibodies (see methods). Both ecNOS and the caveolins were identified in the same extracts (FIG. 4). To show a possible co-localization of ecNOS and the caveolins, immunoprecipitation of ecNOS—caveolin complexes were performed using anticaveolin and anti-ecNOS antibodies. The resulting immuno-complexes were separated by SDS PAGE and were immunoblotted. The immuno-complexes precipitated with anti-caveolin-3 or anti-ecNOS antibody contained both ecNOS and caveolin-3. In contrast, the immuno-complexes precipitated with anti-caveolin- 1 antibody contained only caveolin-1. The data were consistent with the results obtained in cardiomyocytes. In these cells, only caveolin-3 co-precipitated with ecNOS. Most of the ecNOS is membrane bound in bladder smooth muscle cells. Co-localization with caveolin-3 supports the possibility that, similar to cardiomyocytes, ecNOS is localized in the caveolae of bladder smooth muscle cells and modulates receptor related functions.

Figure 5:
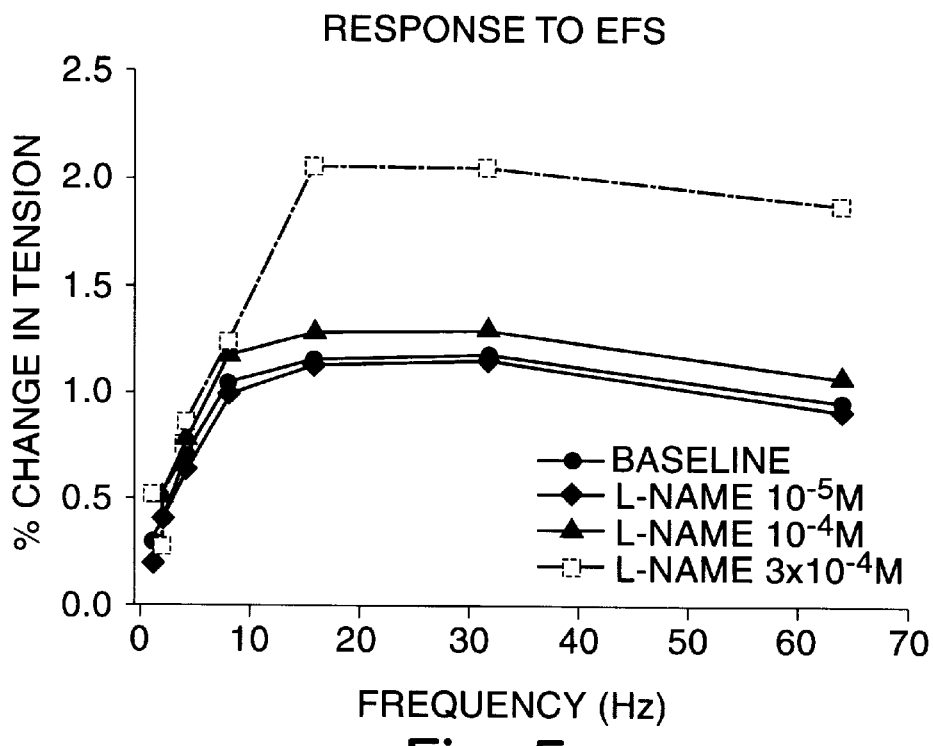
FIG. 5 is a graph depicting the frequency response to electric field stimulation in smooth muscle strips exposed to a nitric oxide synthase (NOS) inhibitor.
Figure 6:
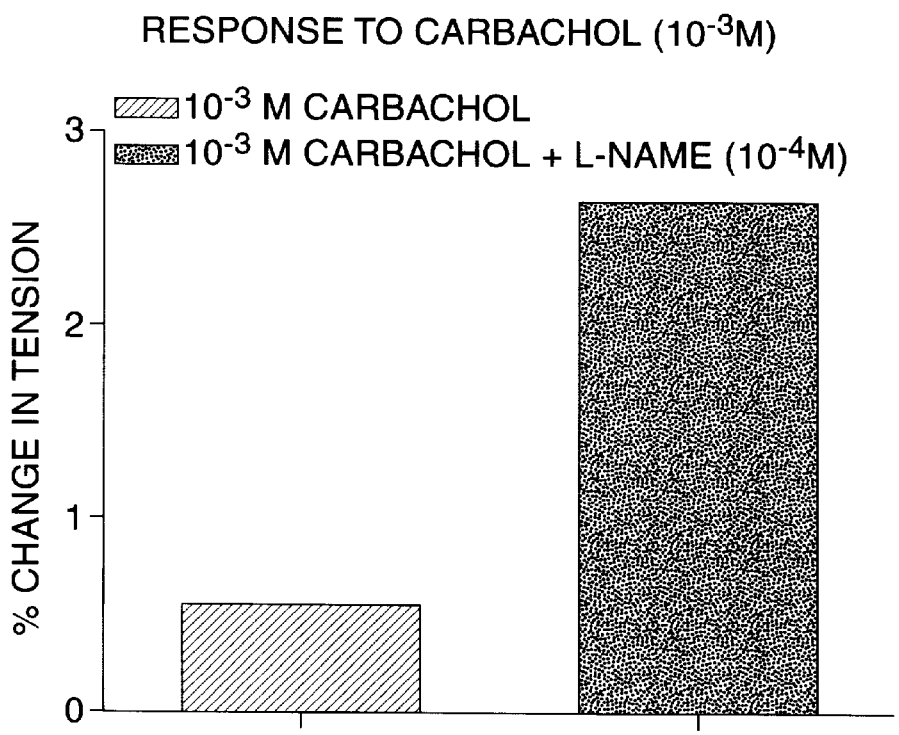
FIG. 6 is a graph depicting the contractile response of smooth muscle strips to carbachol following exposure to an NOS inhibitor.

Effect of L-NAME on bladder smooth muscle contractility. To modify the balance between Angiotensin II and NO production, NO production was suppressed by pre-incubating smooth muscle strips with L-NAME ($10^{-5}$–$10^{-3}$M) for 10 minutes. After this time, the smooth muscle strips were stimulated by EFS (FIG. 5) or carbachol (FIG. 6) and the contractile force development was measured. Pretreatment with L-NAME caused a significant increase in the contractile response to both EFS and carbachol. Furthermore, L-NAME increased the frequency of spontaneous activity in a dose dependent manner. The frequency response to electrical field stimulation was significantly increased in the dome after exposure of the smooth muscle strip to the highest dose of NOS inhibitor (L-NAME, $3\times10^{-4}$M). The contractile response of bladder smooth muscle strips to carbachol ($10^{-3}$M) was also enhanced following exposure to a NOS inhibitor (L-NAME, $3\times10^{-4}$M. We have shown that in the bladder smooth muscle, ecNOS co-precipitates with caveolin-3, and immunohistochemical evidence indicates an accumulation of ecNOS and caveolin-3 adjacent to the plasma membrane. A similar situation was recently described in cardiomyocytes, where NO produced by ecNOS targeted to the caveolae modulates muscarinic receptor activity. Inhibition of ecNOS activity with L-NAME significantly increased the contractile response of bladder smooth muscle to EFS and carbachol. This suggests that NO produced by ecNOS targeted to the caveolae of bladder smooth muscle modulates muscarinic receptor activity. Since NO decreases calcium influx, it has a moderator role. In contrast to this effect, losartan, an $AT_1$ receptor antagonist, decreases bladder smooth muscle responsiveness to EFS or carbachol. Taken together the data presented herein indicate that ecNOS, caveolin-3, the muscarinic receptors of the bladder smooth muscle and Angiotensin II constitute an important regulatory unit of the bladder smooth muscle. Both Angiotensin II and NO modulate muscarinic receptor activity and thereby bladder tone.

Analysis

In NANC nerves NO, produced by bcNOS, serves as a neurotransmitter that mediates the actions of autonomic motor neurons on vascular, gastrointestinal and urogenital smooth muscle. In cardiomyocytes NO, produced by ecNOS, plays an important role in modulation of muscarinic receptor activity by modulating calcium currents generated by muscarinic agonists. This function of NO is assisted by targeting the ecNOS to the caveolae of muscle cells. The caveolae were microdomains of the plasma membrane involved in signal transduction. Muscarinic, adrenergic, endothelin, insulin etc. receptors, ion channels and enzymes, such as protein kinases were targeted to the caveolae. The substrates of the MAP kinases display an agonist binding dependent dynamic translocation into the caveolae. The bladder smooth muscle contains caveolae. In the bladder smooth muscle cells most of the ecNOS and the caveolin-3, a marker protein for caveolae, are plasma membrane- bound. Their co-localization is indicated by their co-precipitation with anti-caveolin-3 or anti-ecNOS antibody in the presence of a detergent. NOS inhibitors modulate smooth muscle contraction in response to electric field stimulation, carbachol or methoxamine, suggesting regulatory interactions between NO and muscarinic or adrenergic receptors.

Example 4: Angiotensin II is a growth factor which modulates proliferation, hypertrophy and remodeling in the bladder.

Methods

Immunohistochemical and chemical quantitation of extracellular matrix proteins. The accumulation of extracellular matrix proteins (collagen type I,III,IV) in the bladder was assessed by immunohistochemical and immunofluorescent techniques similar to the technique used for Angiotensin II. The area and intensity of immunohistochemical reaction were evaluated with video image analysis. The hydroxyproline and protein content of the bladder tissue also was determined.

Electrophoresis and Immunoblots: Proteins from cell lysates, subcellular fractions or the inununoprecipitated proteins were separated on 12% or 7.5% SDS- polyacrylamide gels (SDS-PAGE), transferred to nitrocellulose filters (Schleicher and Schuell, Keene, NH), incubated with blocking solution for 1 h at room temperature (PBS with 0.25% Triton X-100, and 5% dry milk), and then subsequently incubated for 1–3 h with primary and secondary antibodies conjugated with horseradish peroxidase, diluted in blocking solution. Chemiluminescence is developed with the ECL system as described by the manufacturer (Arnersham International, Buckinghamshire, England). We will use our ML 3000 Dynatech luminometer and a special attachment to quantitate the immunoblots. The protein concentration is measured using the Micro BCA protein reagent kit (Pierce Chemical Co., Rockford, Ill.), or Bio-Rad DC assay.

Preparation of caveolae Caveolae were prepared by one of three protocols currently used: a) a detergent free method, b)

immunoprecipitation with an anti caveolin antibody, and c) the carbonate method. For method a) bladder smooth muscle cells were homogenized in 0.25 M sucrose, 1 mM EDTA, 20 mM HEPES, pH 7.4 with protease inhibitors. The post-nuclear supernatant was layered on 30% Percoll and centrifuged at 84.000×g for 30 minutes. After sonication, the upper plasma membrane fraction was mixed with OptiPrep in a final concentration of 23%, layered below a 20–10% OptiPrep gradient, and centrifuged at 52.000×g for 90 minutes. Fractions from this gradient were analyzed by Western blot. Fractions were used to detect caveolin-1 and 3, ecNOS, Angiotensin II receptor, Ras, Raf, and MAP kinase substrates.

Cell stimulation and preparation of cellular lysate. Cells were incubated in Hanks' buffered saline solution (HBSS) containing 10 mM glucose, 1% bovine serum albumin (BSA) 0.5 mM $CaCl_2$ and 0.5 mM $MgCl_2$ for 30 min and then stimulated with agonist or vehicle for 10 min. The reaction was terminated by rapid aspiration of medium, followed by washing with ice-cold NLB buffer containing 20 mM HEPES (pH 7.3), 500 mM NaCl, 50 mM NaF, 5 mM EDTA, 1 mM $Na_3VO_4$, glycerol 10%, protease inhibitors (10 microgram/ml each of leupeptin, trasylol, calpain II inhibitor, pepstatin and pefabloc 1 mg/ml) 1% Triton X-100 and 60 mM n-octyl beta-D-glucopyranosoide. After washing, the cells were solubilized in NLB buffer by assing repeatedly through a 21-gauge needle. The solubilized cell lysate was used for immunoprecipitation. In some experiments washed cells were solubilized by addition of 100 microliter of 2x concentrated SDS-PAGE sample buffer and heating to 100° C. for 3 min (total cell lysatum). For experiments in which cytosol and particulate fractions were separated, the cells were homogenized in NLB buffer (without detergents). One-ml aliquots were ultracentrifuged (Beckman TL100) at 105.000×g for 45 min.

Immunoprecipitation (IP). Cells were lysed in NLB-buffer containing protease inhibitors, 60 mM octylglucoside, and 1% Triton X-100. Aliquots of cell lysates (150 microgram protein) were incubated with the mouse anti-caveolin-3 or anti-caveolin-1 IgG (Transduction Laboratories) at a final concentration of 4 microgram/ml for 1 h at 4° C., followed by addition of anti-mouse IgG for 30 min. For the immunoprecipitation of ecNOS we used rabbit anti-eNOS polyclonal antibody. Negative controls for the mouse monoclonal antibodies use nonimmune mouse IgG. Protein A-Sepharose beads were then added for a further incubation of 1 h at 4° C. Bound immune complexes were washed three times with immunoprecipitation buffer and the pellet is eluted by 2x Laemmli sample buffer by boiling for 5 min. The supernatant protein was separated on SDS-PAGE, transferred on nitrocellulose filters and immnunoblotted with anti-caveolin or anti ecNOS IgG (rabbit or mouse). Fractions were used to detect caveolin-1 and -3, Angiotensin II receptor, ecNOS, Ras, Raf, MAP kinase substrates.

MAP kinase assay. 15 microliters of cytosol fractions or immuno complex suspension (IP with anti $ERK_2$) were assayed for MAP kinase activity using BIOTRAK MAP kinase enzyme assay kit of Amersham. The protein phosphatase activity was suppressed by vanadate.

Measurement of inositol phosphate. Confluent bladder smooth muscle cells were labeled overnight with [$^3$H] inositol~, 10 $\mu$Ci/$10^6$ cells, in medium 199 with 10 $\mu$l/ml penicillin-streptomycin, 10 mM HEPES ph 7.5, and 15% bovine serum, then washed with Hanks' balanced salt solution (HBSS), containing 10 mM LiCl, 0.5 mM $MgSO_4$, 0.5 mM $CaCl_2$ 1% BSA and 10 mM glucose. After washing the cells were then incubated with Angiotensin II ($10^{-6}$ M), or carbachol ($10^{-7}$–$10^{-5}$ M), or methoxamine ($10^{-7}$–$10^{-5}$ M) dissolved in the same HBSS for 30 minutes. The inositol phosphate levels were determined as previously described.

Bladder smooth muscle strip studies. Bladders are obtained as describe above from rats subjected to various combinations of treatment conditions: high sodium diet, low sodium diet, bladder outlet obstruction, chronic administration of losartan or ACE inhibitors. Under a dissecting microscope, the muscle strip are isolated, measured and mounted in a perfusion chamber. One end of the strip is attached to a fixed hook, and the other to a microtransducer capable of measuring tension development. Platinum electrodes will be arranged on both sides of the muscle strip to facilitate electrical field stimulation. Smooth muscles strips from the dome and the base are placed under 2 grams of tension and allowed to equilibrate. The contractile force generated are determined in response to electric field stimulation (10V, 5 msec) over a range of frequencies (1, 2, 4, 8, 32, 64 Hz), carbachol ($10^{-9}$–$10^{-3}$M), methoxamine ($10^{-8}$–$10^{-3}$M), and extracellular potassium (3.5, 10, 20, 40, 60, 80 mM). These responses are determined before and after exposure to an Angiotensin II receptor antagonist (losartan $10^{-5}$–$10^{-3}$M). In addition, the frequency and amplitude of spontaneous activity are determined before and after exposure to losartan ($10^{-5}$–$10^{-3}$M).

Measurement of $Ca_i$ using cell population system: Bladder smooth muscle cell suspensions or confluent primary cultures of bladder smooth muscle grown on coverslips were loaded with fura-2/AM and placed into thermostated cuvettes equipped with a magnetic stirrer, as described previously. The bath solution is stirred at 37° C., and CaR agonists were added to the desired final concentration. Excitation monochromators were centered at 340 nm and 380 nm with emission light collected at 90° using a long-pass emission filter. The 340/380 excitation ratio of emitted light are used to calculate $Ca_i$ as described previously. Both in vivo and in vitro calibrations are used to estimate $Ca_i$.

Results

Figure 7:
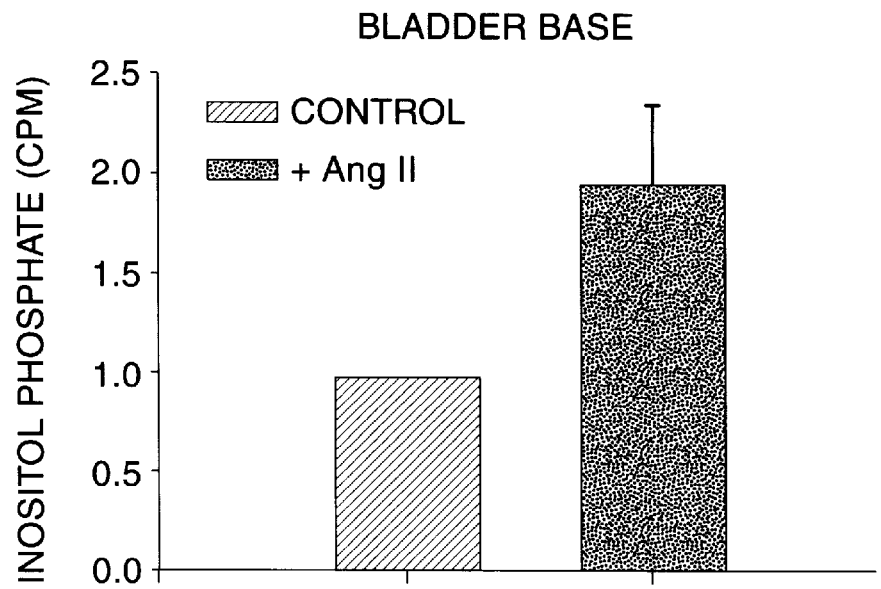
FIG. 7 is a bar graph demonstrating the activation of phospholipase C (PLC) by Angiotensin II generated $IP_3$.

Effect of Angiotensin II, losartan and carbachol on inositol phosphate production: Both muscarinic and $AT_1$ receptors were G protein linked receptors. Thus, the signal transduction pathway activated by muscarinic agonists and Angiotensin II involves the activation of PLC and production of inositol phosphates ($IP_3$). Subsequently, cytosolic calcium levels increase by a complex mechanism that includes calcium influx through the L type channels. High cytosolic calcium modulates smooth muscle tone and the secretory process. Activation of phospholipase C (PLC) by angiotensin II generated [$^3$H] inositol 1, 4, 5 triphosphate ($IP_3$) in our experiments performed in the presence of lithium. $IP_3$ plays an important role in mobilization of calcium from intracellular stores. Both Angiotensin II and carbachol increased inositol phosphate production by primary smooth muscle cell cultures from rat bladder dome and base (FIG. 7). The increased $IP_3$ production in response to Angiotensin II indicates the existence of this signaling pathway in bladder smooth muscle cells. In the presence of losartan, the baseline inositol phosphate production decreased, indicating that the smooth muscle cell cultures constantly release Angiotensin II into the medium.

Figure 8:
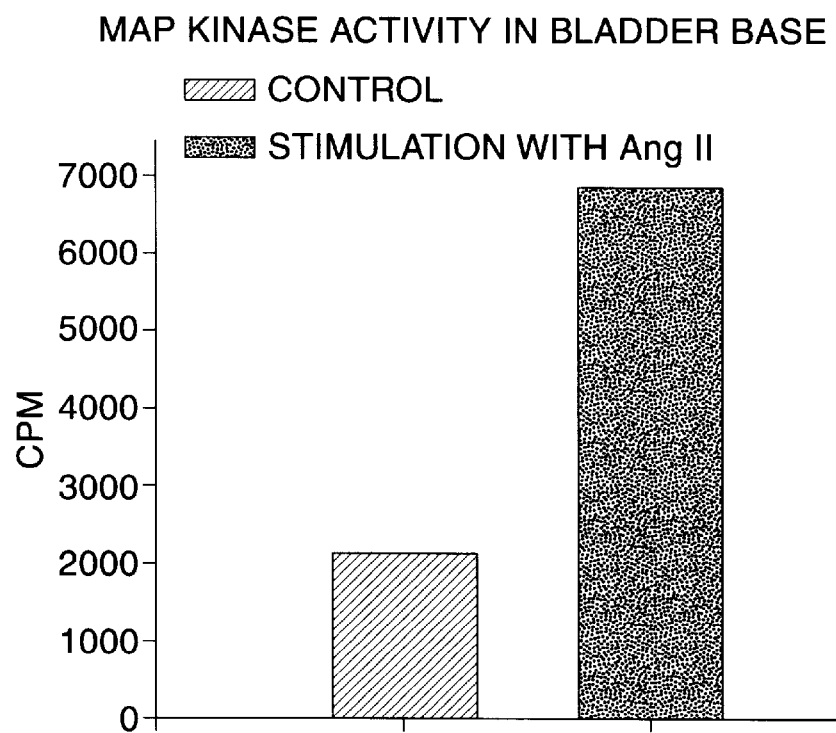
FIG. 8 is a bar graph depicting MAP Kinase activity in bladder smooth muscle cells obtained from the bladder base.
Figure 9A:
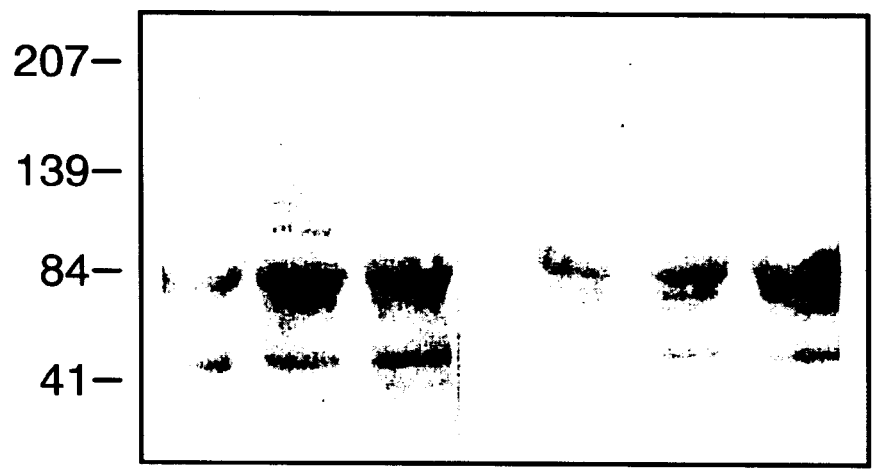
FIG. 9 shows two gels used to determine phosphorylation of MAP Kinase substrates in the cytosol (Panel A) and in the membrane fraction (Panel B).
Figure 9B:
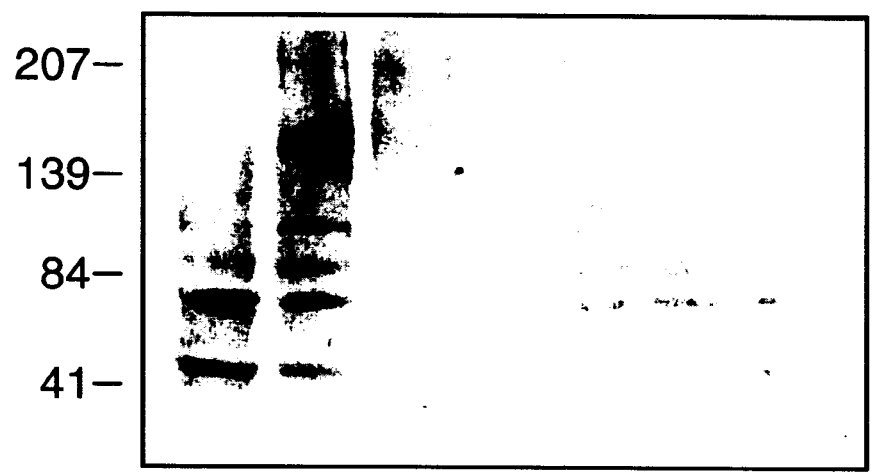

Mitogen activated protein (MAP) kinase activation: Angiotensin II is a growth factor by itself and stimulates the production and secretion of other growth factors. In primary cultures of bladder smooth muscle cells obtained from the base, Angiotensin II ($10^{-6}$M) doubled MAP kinase activity (FIG. 8). This effect was weaker in the dome. An experiment, shown in FIG. 9, was performed to determine the extent of phosphorylation of MAP kinase substrates in the cytosol (Panel A) and in the membrane fraction (Panel B) in the presence or absence of treatment with Angiotensin II. Columns 1–3 were prepared from bladder base, columns 4–6 were prepared from dome. Columns 1 and 4 are controls; columns 2 and 5 are samples treated with vanadate; columns 3 and 6 were exposed to angiotensin II. The molecular weight of markers are represented in kDs on the left side of the panels (e.g., 207, 139, 84, and 47). Vanadate significantly increased the amount of phosphorylated products (columns 2 and 5) by inhibiting phosphatases. Angiotensin II also increased the amount of phosphorylated products. We identified some phosphorylated substrates of MAP kinase. ERK2/MAP kinase with a molecular weight of 42 kD was positively identified as a phosphorylated product. The amount of phosphorylated ERK2 was increased by Angiotensin II in the cytosol of smooth muscle cells obtained from bladder dome or base (FIG. 9). Again, similar to the Angiotensin II induced $IP_3$ production, the Angiotensin II induced MAP kinase activity was stronger in the base. In total cell lysates, the amount and diversity of phosphorylated substrates (including ERK2) was larger. The vanadate increased the amount of phosphorylated substrates of MAP kinases both in the cytosol and membrane fraction, while Angiotensin II increased the level in the cytosol and decreased the level in the membrane fraction, suggesting a translocation of phosphorylated substrates in the base. In the dome the overall phosphorylation was weaker and no apparent translocation was seen.

Figure 10:
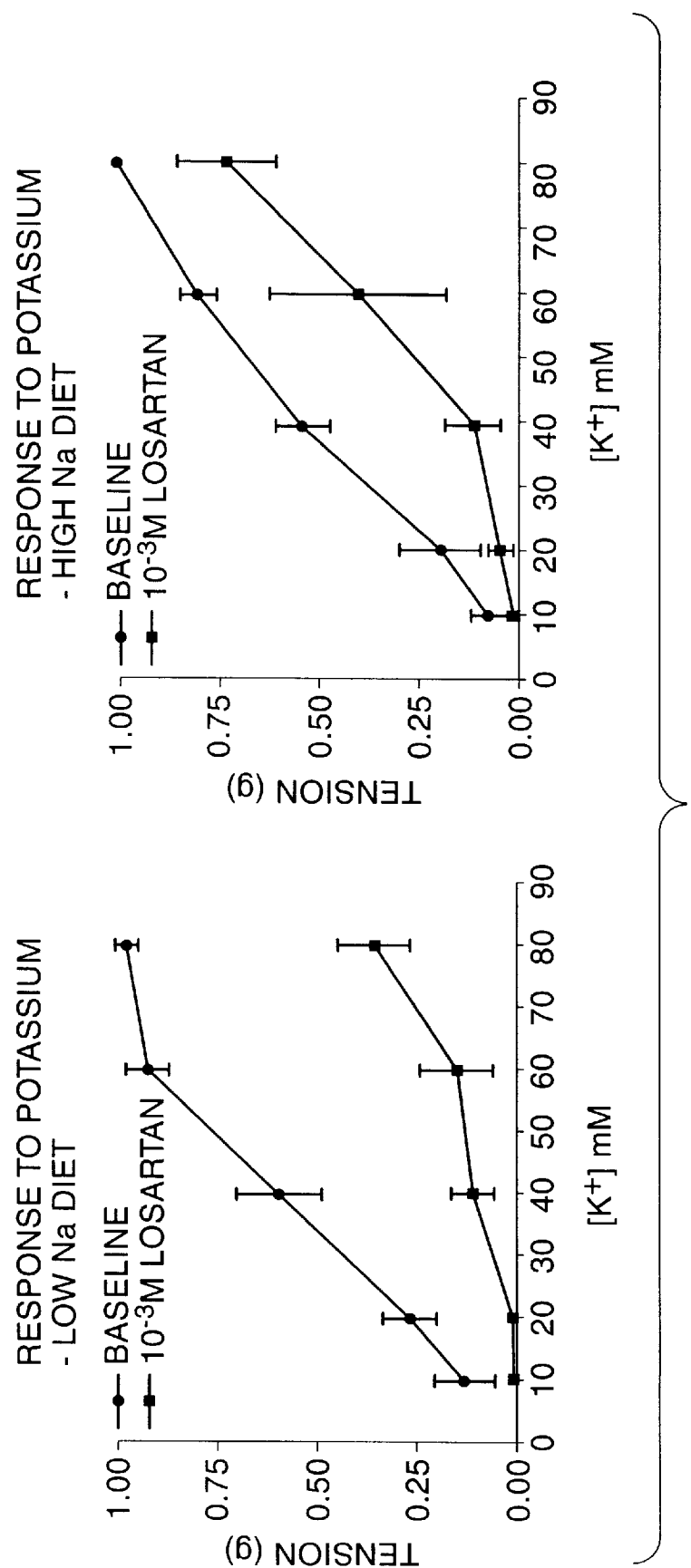
FIG. 10 is a graph depicting the contractile response to potassium in rats fed a low sodium diet (Panel A) and rats fed a high sodium diet (Panel B).

Effect of Angiotensin II on bladder hypertrophy: Angiotensin II is involved in initiation of cell proliferation, hypertrophy and extracellular matrix protein production. An interesting condition that modulates the hypertrophic effect of Angiotensin II is the level of sodium intake. Experimental cardiac fibrosis, i.e. accumulation of extracellular matrix proteins, can be produced only in animals kept on a high sodium diet. A low sodium intake can prevent the development of this condition. ACE inhibitors and Angiotensin II receptor antagonists show a protective effect. The data demonstrate that dietary sodium intake (low sodium diet= 0.2% Na, high sodium diet=1.6% Na) had a significant effect on the response of bladder smooth muscle strips to electric field stimulation, carbachol and high extracellular potassium (FIG. 10). Sodium intake also influenced the suppressive effect of losartan on the frequency dependent contractions generated by electric field stimulation. Both the contractile response to extracellular potassium and the effect of losartan on potassium stimulated contractions were sodium intake dependent. The effect of losartan on the contractile response to extracellular potassium was more pronounced in bladder strips obtained from animals kept on a low sodium diet for 5 days (FIG. 10).

Figure 11:
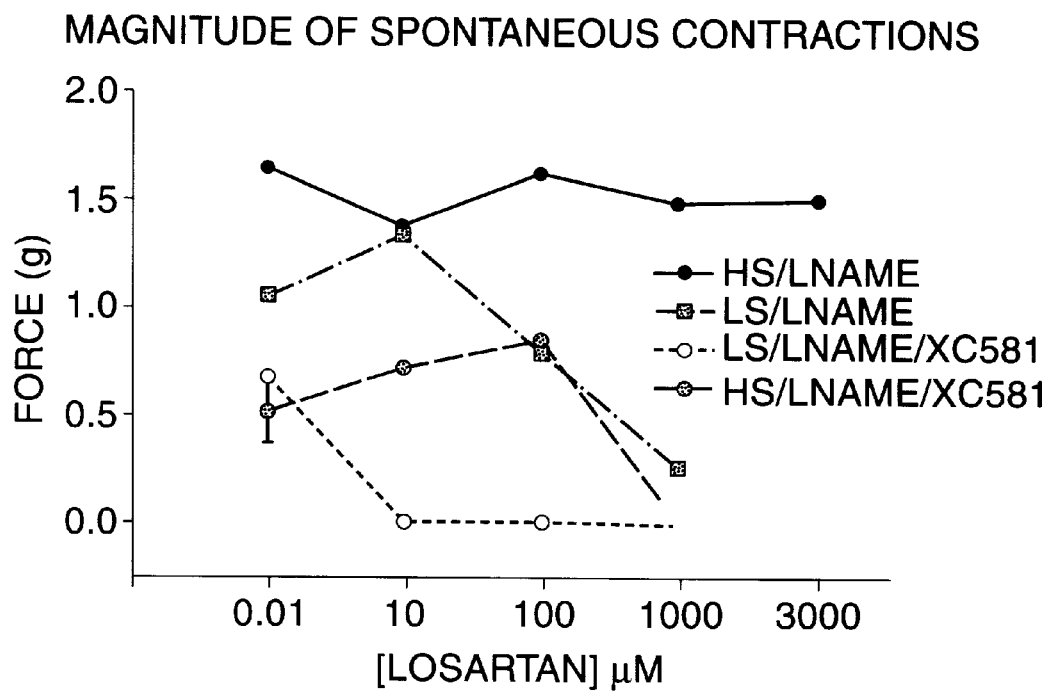
FIG. 11 is a graph depicting the magnitude of spontaneous contractions in bladder smooth muscle strips.

We developed two experimental models of bladder hypertrophy. In one model, we created a partial bladder outlet obstruction in the rat using a silver ring around the urethra. Under sterile conditions, the bladder and proximal urethra of the anesthetized rat were exposed through a midline incision. The prostate was separated from the bladder by carefully cutting the fascia to expose the bladder neck region. A sterile 1.0 mm silver wire ring was placed around the proximal urethra. Then the abdominal muscle and skin were closed in two layers. In a second model, we accelerated the obstruction induced hypertrophy by administering L-NAME daily for five days. For both models, rats were kept on either a high (1.6%) or low (0.2%) sodium diet. In addition, an Angiotensin II antagonist (SC581, Merck-DuPont) was chronically administered in half of the rats. After 7 days, we measured the amplitude of the spontaneous contractile activity of the bladder dome in the presence of increasing concentrations of losartan. The bladder smooth muscle of rats receiving a high Na diet (HS) and L-NAME did not respond to external losartan (FIG. 11). In contrast, the bladder strips obtained from animals that received high Na diet, LNAME and an Angiotensin II receptor antagonist showed a good responsiveness to higher doses of losartan which significantly decreased the magnitude of the spontaneous activity. The bladder strips obtained from animals kept on a low Na diet and L-NAME showed a lower amplitude of spontaneous activity and were responsive to higher doses of losartan. In contrast to the other groups, animals treated with low Na diet and L-NAME and Angiotensin II receptor antagonist showed a low baseline amplitude of spontaneous activity which was completely suppressed by the lowest dose of losartan. These results were consistent with observations that the development of cardiac fibrosis is enhanced by high sodium intake and is suppressed by low sodium intake, Angiotensin II receptor antagonists or ACE inhibitors and aldosterone antagonists. Our observations indicate that the role of high sodium diet in promoting functional changes in smooth muscle is not limited to the cardiovascular system.

Figure 12:
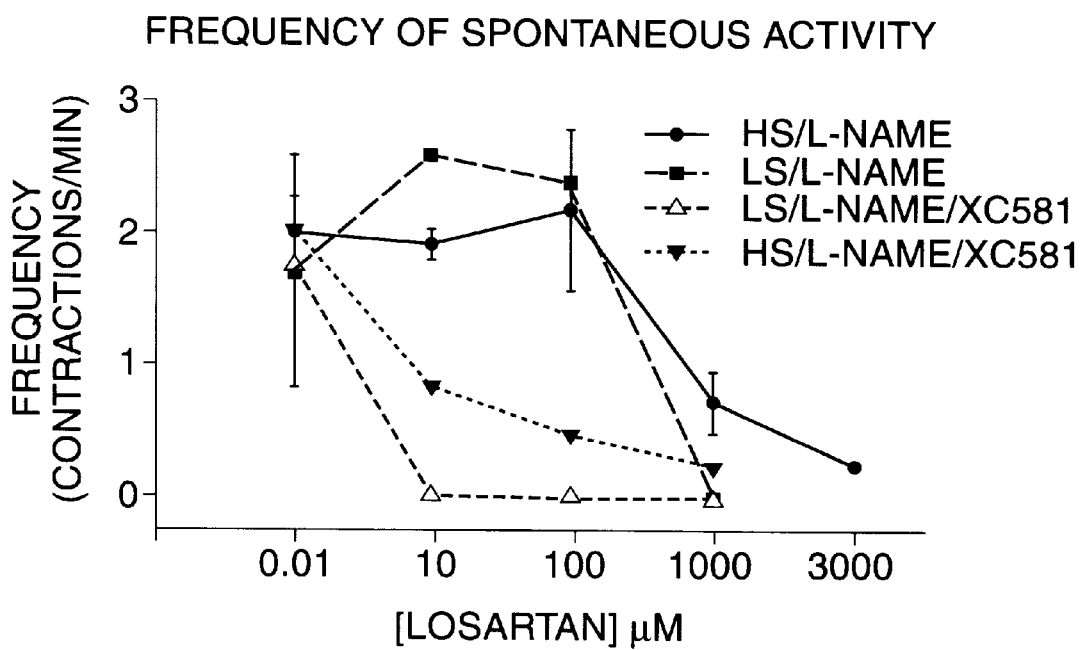
FIG. 12 is a graph depicting the frequency of spontaneous contractions in bladder smooth muscle strips.

Using the same animal models, we determined the frequency of spontaneous activity of bladder smooth muscle strips (FIG. 12). In sodium depleted rats (LS) treated with L-NAME and an Angiotensin II receptor antagonist (XC581), a low dose of losartan was sufficient to eliminate the spontaneous activity. On a high sodium diet (HS), a shift to the right was noticed. The frequency of the spontaneous activity is more sensitive to losartan than the amplitude. Higher doses of losartan decreased the frequency of spontaneous activity regardless of the treatment model (FIG. 12). Similar to the amplitude of spontaneous activity, the frequency of spontaneous activity in rats kept on a low sodium diet, L-NAME and Angiotensin II receptor antagonist was completely abolished by low doses of losartan. A chronic administration of an Angiotensin II receptor antagonist dramatically increased the sensitivity of smooth muscle strips to losartan.

Figure 13:
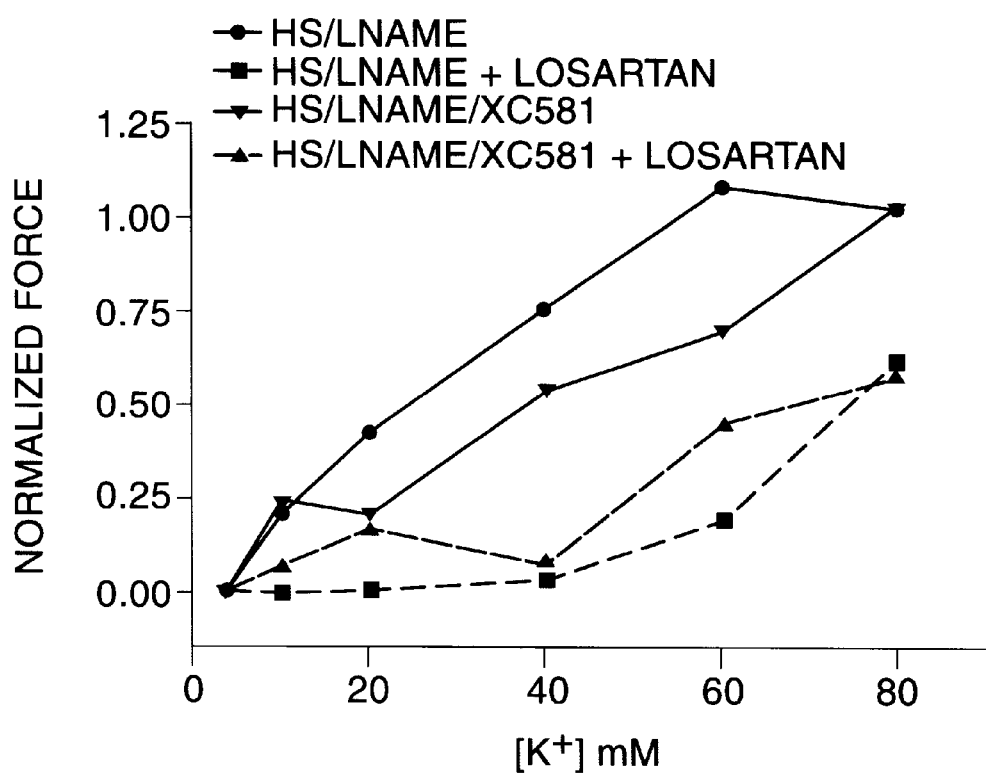
FIG. 13 is a graph depicting the contractile response to extracellular potassium in rat models of bladder obstruction.

Using the same animal models of obstruction and the concept that bladder smooth muscle secretes Angiotensin II which modulates its own contractility, we determined the response of smooth muscle strips to increasing concentrations of potassium (FIG. 13). In sodium loaded rats (HS) treated with L-NAME, administration of losartan to the tissue bath substantially reduced force development in response to increasing [K+]. Bladder smooth muscle strips prepared from rats with a partially obstructed outlet kept on a high sodium diet and L-NAME showed a potassium concentration dependent force development. Administration of losartan into the tissue bath substantially reduced this force development, indicating that high extracellular $K^+$ released Angiotensin II from smooth muscle, which participated in the generation of contractile force. Chronic administration of Angiotensin II receptor antagonist resulted in a blunted response to both extracellular potassium and losartan.

Statistical analysis: Most of the data was analyzed using either paired t or unpaired t tests and ANOVA for normally distributed data or Fisher exact test, Wilcoxon rank sum or sign tests for non-parametric data. The normality of data is tested by the Kolmogorov-Smirnov test. The significance of biologic response curves were assessed by regression analysis. The analysis of variance with a correction for comparison of multiple responses to a single control is performed by using the Dunnett test.

Analysis

Angiotensin II, as a growth factor by itself, initiates a number of signal transduction pathways such as the MAP kinase cascade that activate growth or proliferation related genes. In the cardiovascular system, the growth promoting effect of Angiotensin II is independent of pressure regulation and is responsible for cell proliferation, hypertrophy and accumulation of extracellular matrix proteins, i.e. "cardiovascular remodeling", in a variety of clinical and experimental conditions. Cell proliferation and hypertrophy is controlled by a complex matrix of regulators with variable temporal concentration profiles. In this integrated system Angiotensin II plays a major role by modulating the production and secretion of other growth factors such as the TGFβ, known to be involved in regulation of extracellular matrix protein accumulation. Decreasing Angiotensin II production or its effects by ACE inhibitors or Angiotensin II receptor antagonists prevents cell proliferation, hypertrophy and accumulation of extracellular matrix proteins both in experimental and clinical conditions. For example, administration of ACE inhibitors prevents the development of diabetic nephrosclerosis or the development of scar tissue in the heart after myocardium infarct.

An overproduction or an alteration of Angiotensin II secretion can be experimentally achieved in a wide variety of organs by systemic administration of competitive NOS inhibitors, such as L-NAME. Experimental nephrosclerosis with significant accumulation of extracellular matrix proteins can be produced in the rat in 5 days of L-NAME and Angiotensin II treatment. Our preliminary studies suggests that chronic administration of Angiotensin II receptor antagonists prevent the effects of L-NAME and experimental outlet obstruction on bladder smooth muscle responsiveness.

Dietary sodium intake modulates the effect of Angiotensin II in the regulation of extracellular matrix protein accumulation. A high sodium intake promotes vascular remodeling and extracellular matrix protein accumulation, while a low sodium intake has a preventive effect. Our studies indicate that dietary sodium intake has a great impact on the bladder smooth muscle contraction in response to stimulation.

Functional overload results in smooth muscle stretch that can activate Angiotensin II secretion. Since the stretch related release of Angiotensin II has a different pattern than the neurotransmitter stimulated release, the signal transduction cascade may activate growth related genes. Stretch activated secretion of Angiotensin II from cardiomyocytes promotes hypertrophy. This can be prevented by ACE inhibitors or Angiotensin II receptor antagonists. The secretion of nerve growth factor from bladder smooth muscle cells is also stretch dependent. This suggests that bladder smooth muscle cell plasma membranes contain calcium modulating stretch receptors that control Angiotensin II secretion.

Each of the foregoing patents, patent applications and references is incorporated by reference in its entirety herein by reference. It should be understood that various changes and modification of the embodiment described above may be made within the scope of this invention. Thus, it is intended that all matter contained in the above description shall be interpreted in an illustrative and not limiting sense.

What we claim is:

1. A method for treating bladder dysfunction in a subject, comprising:
    administering to a subject exhibiting symptoms of bladder dysfunction an effective amount of a renin-angiotensin system inhibitor to decrease symptoms of bladder dysfunction, and wherein the amount is one which modifies acutely systemic blood pressure of the subject by less than 10%.

2. The method as claimed in claim 1, wherein the renin-angiotensin system inhibitor is an Angiotensin II antagonist.

3. A method as in claim 2, wherein the Angiotensin II antagonist is Losartan.

4. A method as in claim 2, wherein the therapeutic dose modifies acutely the systemic blood pressure of the subject by less than 5%.

5. A method as in claim 2, wherein the Angiotensin II antagonist is administered orally.

6. A method as in claim 2, wherein the Angiotensin II antagonist is administered by a sustained release implant.

7. A method as in claim 1, wherein the renin-angiotensin system inhibitor is an ACE inhibitor.

8. A method as in claim 1, wherein the renin-angiotensin system inhibitor is a renin inhibitor.

9. A method for preventing bladder dysfunction in a subject, comprising:
    administering to a subject at risk of developing bladder dysfunction an effective amount of a renin-angiotensin system inhibitor to prevent bladder dysfunction, and wherein the amount is one which modifies acutely systemic blood pressure of the subject by less than 10%.

10. The method as claimed in claim 9, wherein the renin-angiotensin system inhibitor is an Angiotensin II antagonist.

11. A method as in claim 10, wherein the Angiotensin II antagonist is Losartan.

12. A method as in claim 10, wherein the therapeutic dose modifies acutely the systemic blood pressure of the subject by less than 5%.

13. A method as in claim 10, wherein the Angiotensin II antagonist is administered orally.

14. A method as in claim 10, wherein the Angiotensin II antagonist is administered by a sustained release implant.

15. A method as in claim 9, wherein the renin-angiotensin system inhibitor is an ACE inhibitor.

16. A method as in claim 9, wherein the renin-angiotensin system inhibitor is a renin inhibitor.

17. A method for treating bladder hypertrophy and remodeling in a subject, comprising:
    administering to a subject having bladder hypertrophy and remodeling an effective amount of a renin-angiotensin system inhibitor to reduce bladder hypertrophy and remodeling, and wherein the amount is one which modifies acutely systemic blood pressure of the subject by less than 10%.

18. The method as claimed in claim 17, wherein the renin-angiotensin system inhibitor is an Angiotensin II antagonist.

19. A method as in claim 18, wherein the Angiotensin II antagonist is Losartan.

20. A method as in claim 18, wherein the therapeutic dose modifies acutely the systemic blood pressure of the subject by less than 5%.

21. A method as in claim 18, wherein the Angiotensin II antagonist is administered orally.

22. A method as in claim 18, wherein the Angiotensin II antagonist is administered by a sustained release implant.

23. A method as in claim 17, wherein the renin-angiotensin system inhibitor is an ACE inhibitor.

24. A method as in claim 17, wherein the renin-angiotensin system inhibitor is a renin inhibitor.

25. A method for treating bladder dysfunction in a subject comprising:

administering to a subject exhibiting symptoms of bladder dysfunction, an effective amount of an $AT_1$ specific Angiotensin II antagonist and an Angiotensin II agonist to decrease the symptoms of bladder dysfunction.

26. A method for reducing the risk of acquiring bladder dysfunction in a subject comprising:

administering to a subject at risk of developing bladder dysfunction, an effective amount of an $AT_1$ specific Angiotensin II antagonist and an Angiotensin II agonist to reduce the risk of acquiring bladder dysfunction.

27. A method for treating bladder hypertrophy and remodeling in a subject comprising:

administering to a subject having bladder hypertrophy and remodeling, an effective amount of an $AT_1$ specific Angiotensin II antagonist and an Angiotensin II agonist to reduce bladder hypertrophy and remodelling.

28. A pharmaceutical composition, comprising:

an $AT_1$ specific Angiotensin II antagonist, an Angiotensin II agonist, and a pharmaceutically acceptable carrier, wherein the $AT_1$ specific Angiotensin II antagonist and the Angiotensin II agonist are present in an effective dose for treating bladder dysfunction.

* * * * *